US012799495B2

(12) United States Patent
Tang et al.

(10) Patent No.: US 12,799,495 B2
(45) Date of Patent: Nov. 17, 2026

(54) GENE KWE2 FOR REGULATING CORN EAR GRAIN WEIGHT AND YIELD, ENCODED PROTEIN, InDel1 MARKER, EXPRESSION VECTOR AND USE THEREOF IN PLANT TRAIT IMPROVEMENT

(71) Applicant: HENAN AGRICULTURAL UNIVERSITY, Zhengzhou (CN)

(72) Inventors: Jihua Tang, Zhengzhou (CN); Zhiyuan Fu, Zhengzhou (CN); Dong Ding, Zhengzhou (CN); Weihua Li, Zhengzhou (CN); Yafei Wang, Zhengzhou (CN); Jun Zong, Zhengzhou (CN)

(73) Assignee: HENAN AGRICULTURAL UNIVERSITY (CN)

( * ) Notice: Subject to any disclaimer, the term of this patent is extended or adjusted under 35 U.S.C. 154(b) by 0 days.

(21) Appl. No.: 18/800,014

(22) Filed: Aug. 10, 2024

(65) Prior Publication Data

US 2025/0059554 A1 Feb. 20, 2025

Related U.S. Application Data

(63) Continuation of application No. PCT/CN2023/093126, filed on May 10, 2023.

(30) Foreign Application Priority Data

May 14, 2022 (CN) ........................ 202210524175.7

(51) Int. Cl.

*C12Q 1/6895* (2018.01)
*C07K 14/415* (2006.01)
*C12N 15/82* (2006.01)

(52) U.S. Cl.

CPC ........ *C12N 15/8261* (2013.01); *C07K 14/415* (2013.01); *C12Q 1/6895* (2013.01); *C12Q 2600/13* (2013.01); *C12Q 2600/156* (2013.01)

(58) Field of Classification Search

None

See application file for complete search history.

(56) References Cited

U.S. PATENT DOCUMENTS

2021/0079410 A1 3/2021 Yang et al.

FOREIGN PATENT DOCUMENTS

| | | |
|---|---|---|
| CN | 107164347 | 9/2017 |
| CN | 112707956 A | 4/2021 |
| CN | 113832179 A | 12/2021 |
| CN | 114958867 A | 8/2022 |

OTHER PUBLICATIONS

Cai et al. Multiomics comparative analysis of the maize large grain mutant tc19 identified pathways related to kernel development. BMC Genomics (2023) 24:537; Published Sep. 11, 2023 (Year: 2023).*

Troyer, F. "Temperate Corn—Background, Behavior, and Breeding." Specialty Coms. CRC Press, 2001. 405-478; Published 2001. (Year: 2001).*

Liu et al. 'Indel Variation in the Maize Genome' BMC Genomics (2015) 16:601; Published Aug. 13, 2015. (Year: 2015).*

International Search Report and Written Opinion of the International Searching Authority dated Oct. 6, 2023,for International Application No. PCT/CN2023/093126, filed May 10, 2023.

Office Action dated Jan. 12, 2023 for Chinese Patent Application No. 202210524175.7.

Notification to Grant Patent Rights for Invention dated Jun. 30, 2023 for Chinese Patent Application No. 202210524175.7.

Shi, X., Zhang, X., Shi, D., Zhang, X., Li, W., & Tang, J. (2019). Dissecting heterosis during the ear inflorescence development stage in maize via a metabolomics-based analysis. Scientific Reports, 9(1), 212.

* cited by examiner

*Primary Examiner* — Anne Kubelik
*Assistant Examiner* — Keith R. Williams
(74) *Attorney, Agent, or Firm* — Kinect Law, PLLC

(57) ABSTRACT

Provided are a gene KWE2 for regulating corn ear grain weight and yield, a protein encoding same, and an expression vector thereof. Further provided are an InDel1 marker of the gene KWE2 for regulating corn ear grain weight and yield, and the use thereof in plant trait improvement.

1 Claim, 11 Drawing Sheets

Specification includes a Sequence Listing.

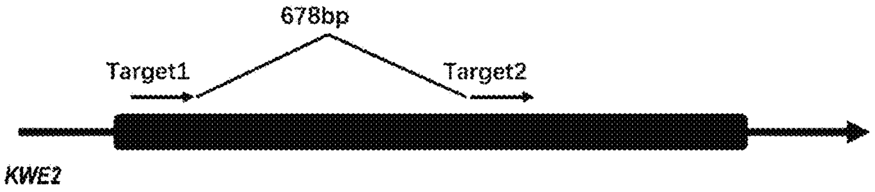

```
Reference : CGGCTCCTGCCCCGACCCGGCCGCGGAAGCG(665)GTGGAAGCTCTTCTCCTGCCCGCTGGACAGGCCTCACCGGGGGC

       WT: CGGCTCCTGCCCCGACCCGGCCGCGGAAGCG(665)GTGGAAGCTCTTCTCCTGCCCGCTGGACAGGCCTCACCGGGGGC    In/Del
      KO1: CGGCTCCTGCCCCGACCCGG-----------(665)-------------------------GACAGGCCTCACCGGGGGC    -701bp
       WT: CGGCTCCTGCCCCGACCCGG-CCGCGGAAGCG(665)GTGGAAGCTCTTCTCCTGCCCGCTGG-ACAGGCCTCACCGGGGGC
      KO2: CGGCTCCTGCCCCGACCCGGACCGCGGAAGCG(665)GTGGAAGCTCTTCTCCTGCCCGCTGGGACAGGCCTCACCGGGGGC   +1bp   +1bp
```

FIG. 3

A
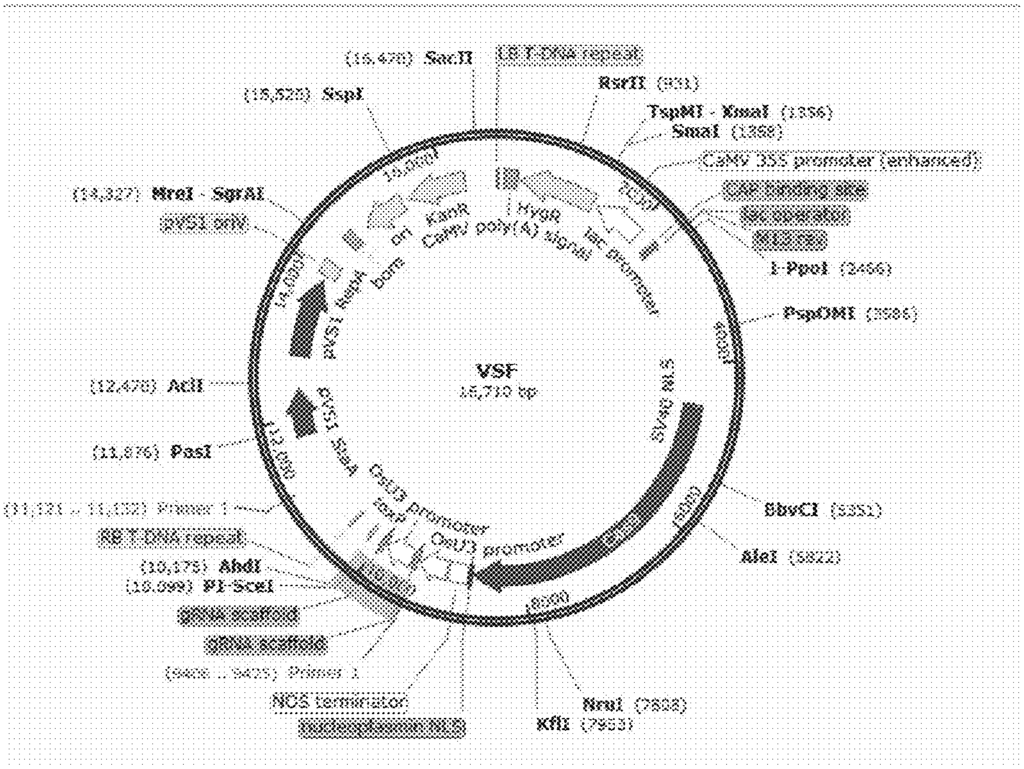
B
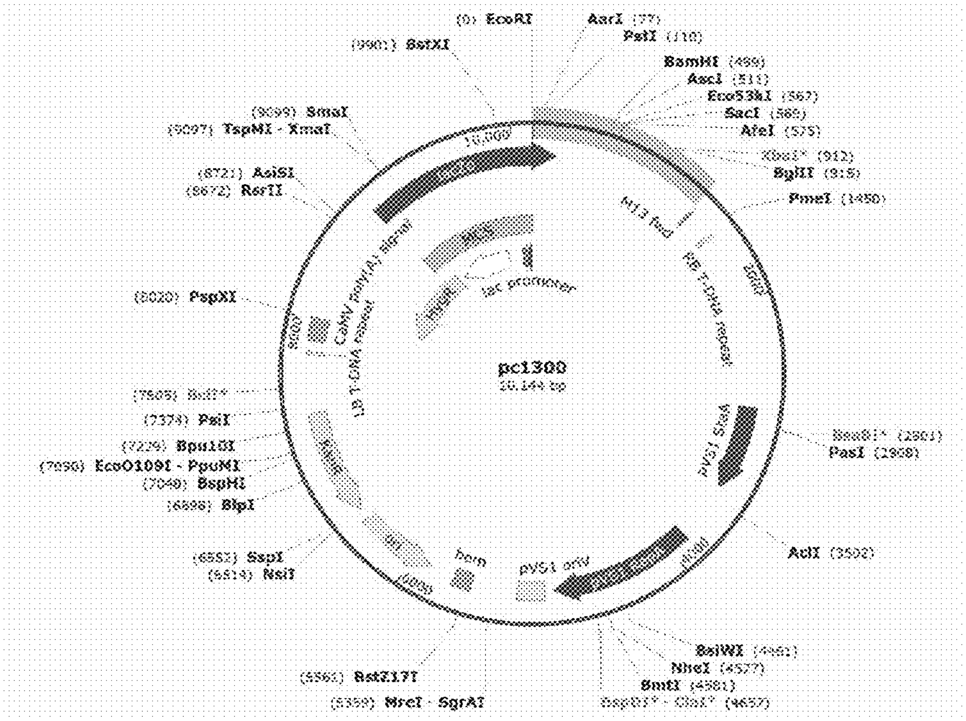
FIG. 9

SEQUENCE LISTING

```
Sequence total quantity: 29
SEQ ID NO: 1           moltype = DNA  length = 2314
FEATURE                Location/Qualifiers
source                 1..2314
                       mol_type = other DNA
                       organism = synthetic construct
SEQUENCE: 1
tatttaacaa accaaataaa aatatgagaa gtgagaagaa gatagatcac gtcattgctc  60
aaaccaaaca accgaacgaa acccgtcgat cagaacccgt gctacccata atgaaagccc  120
atgggcctaa aggcctagcc caccgttctt ctcgtgggac ccacacggag aaccgctctg  180
ccgacaggtg gggtgacccg agccggccag gaaccaacgc gccgcgccgc ccatttgcgg  240
cgtgcatacc ttttatttat cggctaccca acatggcaga cagctgggcc ctggcacgca  300
ttattgcccc acttgccagg cgaagtgagc tgcccaccgc gctcctccgc gtcgctttgc  360
gattttctgg ctcgttccca ccgctgcaac ccggaacttg acgcagtctc tccatgacaa  420
catggcccac aagcgtgggt cccctactca cggactgtac acatatgagg tagagcaata  480
ccgcgtactt acagcccact ccttactttt ttagtttctg tctagttttg atgaggaacg  540
gaaacggaag cgccgctcac caaggcgtaa tgtctaccct tggcctcctt ctcactgaca  600
tccgggtctc ccgcagcacc cacatgggta gaggaaaaac agtgggcagg tcgttctatt  660
ctacggaaac ggaacccaca gcatcgtagg cgaaactgac accctgtccc ccgccttccc  720
cgacctcctc ttcttctcct cgccggcccc cgctatggtc tcatccgtgt gttccccacc  780
taaccccacc ccccaatccg ccatgcccgg cggctcctgc cccgacccgg ccgcggaagc  840
gcagctcccg ccgccgatcc accacctgcc gccggacgcg ctccacaacg tgctgctccg  900
gctgcagctg cgcgacgccg tcgtgtgccg cctcgtctcg cgcctcttcc acgagaccct  960
ctcgccgcag ctcctcgcgc tgctgcccac cctgcgcctc ctcctcctcc gccacccgcg  1020
ccccgacggc ggcggctgcc tccacgcctt cgaccccgcg cgccgcacct ggctccgcct  1080
ccccttcgct cacttcctcc cctaccagtc cttctccccc gtcgcctcat ccacgtccct  1140
cctctacctc tgggtcgaga cctcctcctc cacctcgccc ctagccctcc agtccaccac  1200
tacgtcttcc tccgccgcct cgcccgcgca cccgctcaaa tcgctcgccg tctgcaaccc  1260
cttcgccgga acgtaccgcc tcctgcccca gctcggatcc gcctgggcgc gccacggcac  1320
cgtcctcgcc ggccccggcg gcatggtgct cgtcctcacc gagctcgcag cgctgtccta  1380
cacaccctcc gaatccggca agtggatgaa gcacccgctc tcgctgccgt ccaagccgcg  1440
gagccccata ctggcctccg ccgccgtctt cgccctctgc gacgtcggca cgccgtggcg  1500
cagccagtgg aagctcttct cctgcccgct ggacaggctc accgggggct gggcgcccgt  1560
ggagcgagca gcgtggggag acgtcttcga ggttctcaag cgtcctcggc tccttgccgg  1620
tgccggcggc cgccgggttc ttatggtcgg cgggctcaga tcctcgttcg ccatggacgc  1680
gccgtgctcc accgttctca tactccgtct agatctagcc accatggagt gggacgaagc  1740
tgggcgcatg ccgcccaata tgtaccgctg cttcactggc ctctgcgagg ctgcttcaca  1800
gggcaacgcc atgcctgcca ccgctggcgg gggtaacaat aaggtcaagg ttttcggagg  1860
cgatggaaag gtgtggttcg ctggtaagcg agtgcgcggg aagcttgcaa tgtgggagga  1920
agatgagacg gggagcagtg gcaagtggga ctgggtggat ggtgttcctg gttatgatga  1980
tggtgtgtat cgtggatttg tgttcgatag tggattcaca gcgattcctt gatgcacatg  2040
gaaaacgtat cctagtctgg tgcactcaaa ttgaggttta atttgaccca ggacatctat  2100
ctatcgcatg cacaggatct gttatgccca cacattttat ttacagtctt tagcatggtg  2160
agaactctag ttgttgtact tgattaactg aaaagatcag taagctgttt gtttcagaca  2220
attaaatgct gtagatcata cttgtcagaa acctgatatg ttgctttgat agtgtcagaa  2280
tttttgccat ttggtaaaca ttttctgctt ggtc                              2314

SEQ ID NO: 2           moltype = DNA  length = 2244
FEATURE                Location/Qualifiers
source                 1..2244
                       mol_type = other DNA
                       organism = synthetic construct
SEQUENCE: 2
accgaacgaa acccgtcgat cagaacccgt gctacccata atgaaagccc atgggcctaa  60
aggcctagcc caccgttctt ctcgtgggac ccacacggag aaccgctctg ccgacaggtg  120
gggtgacccg agccggccag gaaccaacgc gccgcgccgc ccatttgcgg cgtgcatacc  180
```

```
ttttatttat cggctaccca acatggcaga cagctgggcc ctggcacgca ttattgcccc  240
acttgccagg cgaagtgagc tgcccaccgc gctcctccgc gtcgctttgc gattttctgg  300
ctcgttccca ccgctgcaac ccggaacttg acgcagtctc tccatgacaa catggcccac  360
aagcgtgggt cccctactca cggactgtac acatatgagg tagagcaata ccgcgtactt  420
acagcccact ccttactttt ttagtttctg tctagttttg atgaggaacg gaaacggaag  480
cgccgctcac caaggcgtaa tgtctaccct tggcctcctt ctcactgaca tccgggtctc  540
ccgcagcacc cacatgggta gaggaaaaac agtgggcagg tcgttctatt ctacggaaac  600
ggaacccaca gcatcgtagg cgaaactgac accctgtccc ccgccttccc cgacctcctc  660
ttcttctcct cgccggcccc cgctatggtc tcatccgtgt gttccccacc taaccccacc  720
ccccaatccg ccatgcccgg cggctcctgc cccgacccgg ccgcggaagc gcagctcccg  780
ccgccgatcc accacctgcc gccggacgcg ctccacaacg tgctgctccg gctgcagctg  840
cgcgacgccg tcgtgtgccg cctcgtctcg cgcctcttcc acgagaccct ctcgccgcag  900
ctcctcgcgc tgctgcccac cctgcgcctc ctcctcctcc gccacccgcg ccccgacggc  960
ggcggctgcc tccacgcctt cgaccccgcg cgccgcacct ggctccgcct cccettcgct  1020
cacttcctcc cctaccagtc cttctccccc gtcgcctcat ccacgtccct cctctacctc  1080
tgggtcgaga cctcctcctc cacctcgccc ctagccctcc agtccaccac tacgtcttcc  1140
tccgccgcct cgcccgcgca cccgctcaaa tcgctcgccg tctgcaaccc cttcgccgga  1200
acgtaccgcc tcctgcccca gctcggatcc gcctgggcgc gccacggcac cgtcctcgcc  1260
ggccccggcg gcatggtgct cgtcctcacc gagctcgcag cgctgtccta cacaccctcc  1320
gaatccggca agtggatgaa gcacccgctc tcgctgccgt ccaagccgcg gagccccata  1380
ctggcctccg ccgccgtctt cgccctctgc gacgtcggca cgccgtggcg cagccagtgg  1440
aagctcttct cctgcccgct ggacaggctc accgggggct gggcgcccgt ggagcgagca  1500
gcgtggggag acgtcttcga ggttctcaag cgtcctcggc tccttgccgg tgccggcggc  1560
cgccgggttc ttatggtcgg cgggctcaga tcctcgttcg ccatggacgc gccgtgctcc  1620
accgttctca tactccgtct agatctagcc accatggagt gggacgaagc tgggcgcatg  1680
ccgcccaata tgtaccgctg ctttactggc ctctgcgagg ctgcttcaca gggcaacgcc  1740
atgcctgcca ccgctggcgg gggtaacaat aaggtcaagg ttttcggagg cgatggaaag  1800
gtgtggtttg ctggtaagcg agtgcgcggg aagcttgcaa tgtgggagga agatgagacg  1860
gggagcagtg gcaagtggga ctgggtggat ggtgttcctg gttatgatga tggtgtgtat  1920
cgtggatttg tgttcgatag tggattcaca gcgattcctt gatgcacatg gaaaacgtat  1980
cctagtctgg tgcactcaaa ttgaggttta atttgaccca ggacatctat ctatcgcatg  2040
cacaggatct gttatgccca cacattttat ttacagtctt tagcatggtg agaactctag  2100
ttgttgtact tgattaactg aaaagatcag taagctgttt gtttcagaca attaaatgct  2160
gtagatcata cttgtcagaa acctgatatg ttgctttgat agtgtcagaa tttttgccat  2220
ttggtaaaca ttttctgctt ggtc                                        2244

SEQ ID NO: 3           moltype = DNA  length = 1625
FEATURE                Location/Qualifiers
source                 1..1625
                       mol_type = other DNA
                       organism = synthetic construct
SEQUENCE: 3
tccgggtctc ccgcagcacc cacatgggta gaggaaaaac agtgggcagg tcgttctatt  60
ctacggaaac ggaacccaca gcatcgtagg cgaaactgac accctgtccc ccgccttccc  120
cgacctcctc ttcttctcct cgccggcccc cgctatggtc tcatccgtgt gttccccacc  180
taaccccacc ccccaatccg ccatgcccgg cggctcctgc cccgacccgg ccgcggaagc  240
gcagctcccg ccgccgatcc accacctgcc gccggacgcg ctccacaacg tgctgctccg  300
gctgcagctg cgcgacgccg tcgtgtgccg cctcgtctcg cgcctcttcc acgagaccct  360
ctcgccgcag ctcctcgcgc tgctgcccac cctgcgcctc ctcctcctcc gccacccgcg  420
ccccgacggc ggcggctgcc tccacgcctt cgaccccgcg cgccgcacct ggctccgcct  480
ccccttcgct cacttcctcc cctaccagtc cttctccccc gtcgcctcat ccacgtccct  540
cctctacctc tgggtcgaga cctcctcctc cacctcgccc ctagccctcc agtccaccac  600
tacgtcttcc tccgccgcct cgcccgcgca cccgctcaaa tcgctcgccg tctgcaaccc  660
cttcgccgga acgtaccgcc tcctgcccca gctcggatcc gcctgggcgc gccacggcac  720
cgtcctcgcc ggccccggcg gcatggtgct cgtcctcacc gagctcgcag cgctgtccta  780
cacaccctcc gaatccggca agtggatgaa gcacccgctc tcgctgccgt ccaagccgcg  840
gagccccata ctggcctccg ccgccgtctt cgccctctgc gacgtcggca cgccgtggcg  900
cagccagtgg aagctcttct cctgcccgct ggacaggctc accgggggct gggcgcccgt  960
ggagcgagca gcgtggggag acgtcttcga ggttctcaag cgtcctcggc tccttgccgg  1020
tgccggcggc cgccgggttc ttatggtcgg cgggctcaga tcctcgttcg ccatggacgc  1080
gccgtgctcc accgttctca tactccgtct agatctagcc accatggagt gggacgaagc  1140
tgggcgcatg ccgcccaata tgtaccgctg cttcactggc ctctgcgagg ctgcttcaca  1200
gggcaacgcc atgcctgcca ccgctggcgg gggtaacaat aaggtcaagg ttttcggagg  1260
cgatggaaag gtgtggttcg ctggtaagcg agtgcgcggg aagcttgcaa tgtgggagga  1320
agatgagacg gggagcagtg gcaagtggga ctgggtggat ggtgttcctg gttatgatga  1380
tggtgtgtat cgtggatttg tgttcgatag tggattcaca gcgattcctt gatgcacatg  1440
gaaaacgtat cctagtctgg tgcactcaaa ttgaggttta atttgaccca ggacatctat  1500
ctatcgcatg cacaggatct gttatgccca cacattttat ttacagtctt tagcatggtg  1560
agaactctag ttgttgtact tgattaactg aaaagatcag taagctgttt gtttcagaca  1620
attaa                                                             1625

SEQ ID NO: 4           moltype = AA  length = 409
FEATURE                Location/Qualifiers
source                 1..409
                       mol_type = protein
                       organism = synthetic construct
SEQUENCE: 4
MPGGSCPDPA AEAQLPPPJH HLPPDALHNV LLRLQLRDAV VCRLVSRLFH ERLSPQLLAL  60
LPRLRLLLLR HPRPDGGGCL HAFDPARRRW LRLPFAHFLP YQSFSPVASS RSLLYLWVER  120
```

-continued

```
SSSRSPLALQ SRRRSSSAAS PAHPLKSLAV CNPFAGRYRL LPQLGSAWAR HGRVLAGPGG  180
MVLVLRELAA LSYRPSESGK WMKHPLSLPS KPRSPJLASA AVFALCDVGR PWRSQWKLFS  240
CPLDRLRGGW APVERAAWGD VFEVLKRPRL LAGAGGRRVL MVGGLRSSFA MDAPCSRVLJ  300
LRLDLARMEW DEAGRMPPNM YRCFRGLCEA ASQGNAMPAR AGGGNNKVKV FGGDGKVWFA  360
GKRVRGKLAM WEEDERGSSG KWDWVDGVPG YDDGVYRGFV FDSGFRAJP             409

SEQ ID NO: 5            moltype = DNA  length = 2053
FEATURE                 Location/Qualifiers
source                  1..2053
                        mol_type = other DNA
                        organism = synthetic construct
SEQUENCE: 5
tttctgttct agtgtcgggt tcattaatgt tcactgttta ttgttgtgta tactactcta  60
ggtcggttca ttgttgtgtt aattccatgt atgttgttgt cactactatt cgttgctttc  120
attgctgtta tctatttatg cacacatgaa ttagattaag atgatgagga catggaattt  180
tttttgaaga gttatgaaca aattgacaat acatatgatg cttggtacgt tacactacga  240
cacatacatg aataaagaat agtatagaaa tccagtcgag tccagtttcc aatgggttat  300
gacatcccta ggtaatacga cagcttgatt caacatgttt aggatgcaca atgatgtgtt  360
ccataaactg cataatgtac tagtggagtc acatggtctg aaatcaacta caaaaatgtc  420
accaattgag gcactaggtc aatatttatg gatgtgtggt gcccctcaaa gtatgagaca  480
tgacgaaaat cgtttttgta gatcaacata tacgcgcagt aagaagttta gtgaagtatt  540
gttaagtgtc aataaacttg cagcagatat tattaagcca ttagatcctg aatttagtct  600
caccatttta gtctcattta gtccctaaat tgccaaacag tgggactaaa atagagacta  660
aacttttttta gtctctagtc tctaaagagg tgactaaaag agactaaact atataaattt  720
taccttttgt ctcttcttta tttcagtaat tttggtcctc ctatggtttc atttaatgcg  780
ttttgaataa ttttagtctt tagaaccaaa cggagtagag actaaactgt agtattctaa  840
ctaaacttta atccctaaac taaagaaatc aaacgggtcc ttagtcacta aactttagtc  900
agcccagaac aaacggggcc taagtgttta cttgtgctta ttcttcaaat agaaaagtaa  960
aaaatcacct tgaaaaccaa ttgtacctag tgcagagagg taaataaaac gacattgaga  1020
gttaaaggac gaaatttgct cggtttcaaa cttcgaatag aaaacttaga tggcaattat  1080
atacaccagt ttagaatcct tctttttat tgtgtttggt ttatggagtc acccaatcat  1140
tttgatgcat cataagttca ttccatcaat tttggtggaa tcaactcact tctcacgtat  1200
atactaatta ttagcttata agaaatgaag tggtgatgga taaacttatt ctatttaaca  1260
aaccaaataa aaatatgaga agtgagaaga agatagatca cgtcattgct caaaccaaac  1320
aaccgaacga aacccgtcga tcagaacccg tgctacccat aatgaaagcc catgggccta  1380
aaggcctagc ccaccgttct tctcgtggga cccacacgga gaaccgctct gccgacaggt  1440
ggggtgaccc gagccggcca ggaaccaacg cgccgcgccg cccatttgcg gcgtgcatac  1500
cttttattta tcggctaccc aacatggcag acagctgggc cctggcacgc attattgccc  1560
cacttgccag gcgaagtgag ctgcccaccg cgctcctccg cgtcgctttg cgattttctg  1620
gctcgttccc accgctgcaa cccggaactt gacgcagtct ctccatgaca acatggccca  1680
caagcgtggg tcccctactc acggactgta cacatatgag gtagagcaat accgcgtact  1740
tacagcccac tccttacttt tttagtttct gtctagtttt gatgaggaac ggaaacggaa  1800
gcgccgctca ccaaggcgta atgtctaccc ttggcctcct tctcactgac atccgggtct  1860
cccgcagcac ccacatgggt agaggaaaaa cagtgggcag gtcgttctat tctacggaaa  1920
cggaacccac agcatcgtag gcgaaactga caccctgtcc cccgccttcc ccgacctcct  1980
cttcttctcc tcgccggccc ccgctatggt ctcatccgtg tgttccccac ctaaccccac  2040
cccccaatcc gcc                                                     2053

SEQ ID NO: 6            moltype = DNA  length = 1844
FEATURE                 Location/Qualifiers
source                  1..1844
                        mol_type = other DNA
                        organism = synthetic construct
SEQUENCE: 6
tttctgttct agtgtcgggt tcattaatgt tcactgttta ttgttgtgta tactactcta  60
ggtcggttca ttgttgtgtt aattccatgt atgttgttgt cactactatt cgttgctttc  120
attgctgtta tctatttatg cacacatgaa ttagattaag atgatgagga catggaattt  180
tttttgaaga gttatgaaca aattgacaat acatatgatg cttggtacgt tacactacga  240
cacatacatg aataaagaat agtatagaaa tccagtcgag tccagtttcc aatgggttat  300
gacatcccta ggtaatacga cagcttgatt caacatgttt aggatgcaca atgatgtgtt  360
ccataaactg cataatgtac tagtggagtc acatggtctg aaatcaacta caaaaatgtc  420
accaattgag gcactaggtc aatatttatg gatgtgtggt gcccctcaaa gtatgagaca  480
tgacgaaaat cgtttttgta gatcaacata tacgcgcagt aagaagttta gtgaagtatt  540
gttaagtgtc aataaacttg cagcagatat tattaagcca ttagatcctg aatttagtct  600
caccatttta gtctcattta gtccctaaat tgccaaacag tgggactaaa atagagacta  660
aacttttttta gtctctagtc tctaaagagg tgactaaaag agactaaact atataaattt  720
taccttttgt ctcttcttta tttcagtaat tttggtcctc ctatggtttc atttaatgcg  780
ttttgaataa ttttagtctt tagaaccaaa cggagtagag actaaactgt agtattctaa  840
ctaaacttta atccctaaac taaagaaatc aaacgggtcc ttagtcacta aactttagtc  900
agcccagaac aaacggggcc taagtgttta cttgtgctta ttcttcaaat agaaaagtaa  960
aaaatcacct tgaaaaccaa ttgtacctag tgcagagagg taaataaaac gacattgaga  1020
gttaaaggac gaaatttgct cggtttcaaa cttcgaatag aaaacttaga tggcaattat  1080
atacaccagt ttagaatcct tctttttat tgaccgaacg aaacccgtcg atcagaaccc  1140
gtgctaccca taatgaaagc ccatgggcct aaaggcctag cccaccgttc ttctcgtggg  1200
acccacacgg agaaccgctc tgccgacagg tggggtgacc cgagccggcc aggaaccaac  1260
gcgccgcgcc gcccatttgc ggcgtgcata ccttttattt atcggctacc caacatggca  1320
gacagctggg ccctggcacg cattattgcc ccacttgcca ggcgaagtga gctgcccacc  1380
gcgctcctcc gcgtcgcttt gcgattttct ggctcgttcc caccgctgca acccggaact  1440
tgacgcagtc tctccatgac aacatggccc acaagcgtgg gtcccctact cacggactgt  1500
```

```
acacatatga ggtagagcaa taccgcgtac ttacagccca ctccttactt ttttagtttc  1560
tgtctagttt tgatgaggaa cggaaacgga agcgccgctc accaaggcgt aatgtctacc  1620
cttggcctcc ttctcactga catccgggtc tcccgcagca cccacatggg tagaggaaaa  1680
acagtgggca ggtcgttcta ttctacggaa acggaaccca cagcatcgta ggcgaaactg  1740
acaccctgtc ccccgccttc cccgacctcc tcttcttctc ctcgccggcc cccgctatgg  1800
tctcatccgt gtgttcccca cctaacccca ccccccaatc cgcc                    1844

SEQ ID NO: 7            moltype = DNA  length = 3649
FEATURE                 Location/Qualifiers
source                  1..3649
                        mol_type = other DNA
                        organism = synthetic construct
SEQUENCE: 7
tttctgttct agtgtcgggt tcattaatgt tcactgttta ttgttgtgta tactactcta  60
ggtcggttca ttgttgtgtt aattccatgt atgttgttgt cactactatt cgttgctttc  120
attgctgtta tctatttatg cacacatgaa ttagattaag atgatgagga catggaattt  180
tttttgaaga gttatgaaca aattgacaat acatatgatg cttggtacgt tacactacga  240
cacatacatg aataaagaat agtatagaaa tccagtcgag tccagtttcc aatgggttat  300
gacatcccta ggtaatacga cagcttgatt caacatgttt aggatgcaca atgatgtgtt  360
ccataaactg cataatgtac tagtggagtc acatggtctg aaatcaacta caaaaatgtc  420
accaattgag gcactaggtc aatatttatg gatgtgtggt gcccctcaaa gtatgagaca  480
tgacgaaaat cgtttttgta gatcaacata tacgcgcagt aagaagttta gtgaagtatt  540
gttaagtgtc aataaacttg cagcagatat tattaagcca ttagatcctg aatttagtct  600
caccatttta gtctcattta gtccctaaat tgccaaacag tgggactaaa atagagacta  660
aactttttta gtctctagtc tctaaagagg tgactaaaag agactaaact atataaattt  720
tacctttgt ctcttcttta tttcagtaat tttggtcctc ctatggtttc atttaatgcg  780
ttttgaataa ttttagtctt tagaaccaaa cggagtagag actaaactgt agtattctaa  840
ctaaacttta atccctaaac taaagaaatc aaacgggtcc ttagtcacta aactttagtc  900
agcccagaac aaacggggcc taagtgttta cttgtgctta ttcttcaaat agaaaagtaa  960
aaaatcacct tgaaaaccaa ttgtacctag tgcagagagg taaataaaac gacattgaga  1020
gttaaaggac gaaatttgct cggtttcaaa cttcgaatag aaaacttaga tggcaattat  1080
atacaccagt ttagaatcct tctttttat tgtgtttggt ttatggagtc acccaatcat  1140
tttgatgcat cataagttca ttccatcaat tttggtggaa tcaactcact tctcacgtat  1200
atactaatta ttagcttatc tctacaacta ttaagactct aatgtagacc actaccgtgc  1260
ctccgctcgc gcttcgcatg caacaacctc cctgcatgca agccgcatgc aagcgacgca  1320
agttgctcaa cctccactgc atgcaagccg catgcaaacc acatgcaagc cacatgcaag  1380
ccgcaagctg ctgcagaacc tgcatgcaag ccgagaagct gctgcatgca agcatcgtgt  1440
ctccctccac tcatgaaacg tcgtggaaat tgaagggggc tggcctggtg gctggctgtt  1500
gtccgtctgt ccctctgcta caagcctgta gtgctgctca gctgttgtcg gctcgatcga  1560
ttcccctacc tgggcagcgc tagccggcta gccctatgga ctcgaggcct gattcgcaat  1620
cttactctta cccactggtc gcagccgctg gtagcatcgt acaatctaca atttccagtt  1680
cgagaataaa atcagctaga taaaaaccac aaatccaaca aaatctaata tgtactcgca  1740
caaaaacaat taccatatat actttttaat ttaggtcatc aaccactatg cactaaggaa  1800
cactaagcaa gcactgacgg ggctgggtgg gaggaaccta gcgaggcgcc acccatcgtg  1860
tttcctctga ggctctgcga tcgtcgttgt cttgttgcat gcactgaggc tgaacgcgct  1920
gctgctactc ctctgcctgt gcgcgttccc cgccccggcg cggtcgcaga acacgaccat  1980
ggccacgacc gcgcaggcgt ccgtcgaggg gttcaactgc accgccaacc gcacgtaccc  2040
atgccaggtg tacgcgctct accgcaccgg cttcgcgggc gtgccgctcg atctcgcggc  2100
catcggtgac ctctttgccg tcagctgctt catggtcgcg cacgccaaca acctctccac  2160
gacggccgcg ctggccaacg gacagccgct gctcgtgccg ctctagtgcg gctgcccctc  2220
ccggtacccc agctcgtacg cgccgatgca gtaccagatc gactcgggga cacctactgg  2280
atcgtctcca ctaccaagct gcagaacctc atgcagtact aggccgtgga gcgcgtgaac  2340
cccacgctgg tgcccaccgt cctcgacgtt ggcaccatgg tcacgttccc cgtcttctgc  2400
cagtgcccgg ccgccgccga caatgccacg acactcgtca cctacgtcat gcagcccggg  2460
gacacgtacg tgtctgttgc cgccgccttc tccgtcgccc atccacagtg aaagacacga  2520
tgcggcggcc gcctgtgcat gcactgaagt tgcgcgctgc tgctgctcct ctgcctatgc  2580
gtgttccccg ccccgatgcg gtcgtagaac acgaccacag ccacgaccaa atttattcaa  2640
ctagatggag ttgaaggctg aaggtacgac gggtgataaa acgatatatg atttgtgcat  2700
gaatatgtgc ttcagcttgt gcaacataac aggttagaaa tttaactatc tgcgtgcggt  2760
tattaatgtc ttagaaattt taactctcgt ggcaacgcac gggcacatat ctagtaagaa  2820
atgaagtggt gatggataaa cttattctat ttaacaaacc aaataaaaat atgagaagtg  2880
agaagaagat agatcacgtc attgctcaaa ccaaacaacc gaacgaaacc cgtcgatcag  2940
aacccgtgct acccataatg aaagcccatg ggcctaaagg cctagcccac cgttcttctc  3000
gtgggaccca cacggagaac cgctctgccg acaggtgggg tgacccgagc cggccaggaa  3060
ccaacgcgcc gcgccgccca tttgcggcgt gcataccttt tatttatcgg ctacccaaca  3120
tggcagacag ctgggccctg gcacgcatta ttgccccact tgccaggcga agtgagctgc  3180
ccaccgcgct cctccgcgtc gctttgcgat tttctggctc gttcccaccg ctgcaacccg  3240
gaacttgacg cagtctctcc atgacaacat ggcccacaag cgtgggtccc ctactcacgg  3300
actgtacaca tatgaggtag agcaataccg cgtacttaca gcccactcct tacttttta  3360
gtttctgtct agttttgatg aggaacggaa acggaagcgc cgctcaccaa ggcgtaatgt  3420
ctacccttgg cctccttctc actgacatcc gggtctcccg cagcacccac atgggtagag  3480
gaaaaacagt gggcaggtcg ttctattcta cggaaacgga acccacagca tcgtaggcga  3540
aactgacacc ctgtcccccg ccttccccga cctcctcttc ttctcctcgc cggcccccgc  3600
tatggtctca tccgtgtgtt ccccacctaa ccccaccccc caatccgcc             3649

SEQ ID NO: 8            moltype = DNA  length = 75
FEATURE                 Location/Qualifiers
source                  1..75
                        mol_type = other DNA
```

```
                        organism = synthetic construct
SEQUENCE: 8
cggctcctgc cccgacccgg ccgcggaagc ggtggaagct cttctcctgc ccgctggaca  60
ggcctcaccg ggggc                                                   75

SEQ ID NO: 9            moltype = DNA  length = 75
FEATURE                 Location/Qualifiers
source                  1..75
                        mol_type = other DNA
                        organism = synthetic construct
SEQUENCE: 9
cggctcctgc cccgacccgg ccgcggaagc ggtggaagct cttctcctgc ccgctggaca  60
ggcctcaccg ggggc                                                   75

SEQ ID NO: 10           moltype = DNA  length = 39
FEATURE                 Location/Qualifiers
source                  1..39
                        mol_type = other DNA
                        organism = synthetic construct
SEQUENCE: 10
cggctcctgc cccgacccgg gacaggcctc accgggggc                         39

SEQ ID NO: 11           moltype = DNA  length = 75
FEATURE                 Location/Qualifiers
source                  1..75
                        mol_type = other DNA
                        organism = synthetic construct
SEQUENCE: 11
cggctcctgc cccgacccgg ccgcggaagc ggtggaagct cttctcctgc ccgctggaca  60
ggcctcaccg ggggc                                                   75

SEQ ID NO: 12           moltype = DNA  length = 77
FEATURE                 Location/Qualifiers
source                  1..77
                        mol_type = other DNA
                        organism = synthetic construct
SEQUENCE: 12
cggctcctgc cccgacccgg accgcggaag cggtggaagc tcttctcctg cccgctggga  60
caggcctcac cgggggc                                                 77

SEQ ID NO: 13           moltype = DNA  length = 22
FEATURE                 Location/Qualifiers
source                  1..22
                        mol_type = other DNA
                        organism = synthetic construct
SEQUENCE: 13
tcctgccccg acccggccgc gg                                           22

SEQ ID NO: 14           moltype = DNA  length = 22
FEATURE                 Location/Qualifiers
source                  1..22
                        mol_type = other DNA
                        organism = synthetic construct
SEQUENCE: 14
cttctcctgc ccgctggaca gg                                           22

SEQ ID NO: 15           moltype = DNA  length = 36
FEATURE                 Location/Qualifiers
source                  1..36
                        mol_type = other DNA
                        organism = synthetic construct
SEQUENCE: 15
aataatggtc tcaggcgtcc tgccccgacc cggccg                            36

SEQ ID NO: 16           moltype = DNA  length = 40
FEATURE                 Location/Qualifiers
source                  1..40
                        mol_type = other DNA
                        organism = synthetic construct
SEQUENCE: 16
gtcctgcccc gacccggccg gttttagagc tagaaatagc                        40

SEQ ID NO: 17           moltype = DNA  length = 33
FEATURE                 Location/Qualifiers
source                  1..33
                        mol_type = other DNA
                        organism = synthetic construct
SEQUENCE: 17
gtccagcggg caggagaagc gcttcttggt gcc                               33
```

```
SEQ ID NO: 18          moltype = DNA  length = 36
FEATURE                Location/Qualifiers
source                 1..36
                       mol_type = other DNA
                       organism = synthetic construct
SEQUENCE: 18
attattggtc tctaaacgtc cagcgggcag gagaag                          36

SEQ ID NO: 19          moltype = DNA  length = 18
FEATURE                Location/Qualifiers
source                 1..18
                       mol_type = other DNA
                       organism = synthetic construct
SEQUENCE: 19
gtcagcccag aacaaacg                                              18

SEQ ID NO: 20          moltype = DNA  length = 18
FEATURE                Location/Qualifiers
source                 1..18
                       mol_type = other DNA
                       organism = synthetic construct
SEQUENCE: 20
ggtcccacga gaagaacg                                              18

SEQ ID NO: 21          moltype = DNA  length = 35
FEATURE                Location/Qualifiers
source                 1..35
                       mol_type = other DNA
                       organism = synthetic construct
SEQUENCE: 21
cagtggtctc aggcaccggc attgccgcag cttat                           35

SEQ ID NO: 22          moltype = DNA  length = 35
FEATURE                Location/Qualifiers
source                 1..35
                       mol_type = other DNA
                       organism = synthetic construct
SEQUENCE: 22
cagtggtctc aaaacataag ctgcggcaat gccgg                           35

SEQ ID NO: 23          moltype = DNA  length = 34
FEATURE                Location/Qualifiers
source                 1..34
                       mol_type = other DNA
                       organism = synthetic construct
SEQUENCE: 23
cagtggtctc aggcaggacg gaggaggcaa atcc                            34

SEQ ID NO: 24          moltype = DNA  length = 34
FEATURE                Location/Qualifiers
source                 1..34
                       mol_type = other DNA
                       organism = synthetic construct
SEQUENCE: 24
cagtggtctc aaaacggatt tgcctcctcc gtcc                            34

SEQ ID NO: 25          moltype = DNA  length = 24
FEATURE                Location/Qualifiers
source                 1..24
                       mol_type = other DNA
                       organism = synthetic construct
SEQUENCE: 25
atacgaagtt atgactgcga ccga                                       24

SEQ ID NO: 26          moltype = DNA  length = 25
FEATURE                Location/Qualifiers
source                 1..25
                       mol_type = other DNA
                       organism = synthetic construct
SEQUENCE: 26
acggtgtcgt ccatcacagt ttgcc                                      25

SEQ ID NO: 27          moltype = DNA  length = 25
FEATURE                Location/Qualifiers
source                 1..25
                       mol_type = other DNA
                       organism = synthetic construct
SEQUENCE: 27
```

-continued

```
ttccggaagt gcttgacatt gggga                                          25

SEQ ID NO: 28          moltype = DNA  length = 21
FEATURE                Location/Qualifiers
source                 1..21
                       mol_type = other DNA
                       organism = synthetic construct
SEQUENCE: 28
agaacagtac catggcgtga c                                              21

SEQ ID NO: 29          moltype = DNA  length = 21
FEATURE                Location/Qualifiers
source                 1..21
                       mol_type = other DNA
                       organism = synthetic construct
SEQUENCE: 29
acgttctgtc aaatctgtcc c                                              21
```

GENE KWE2 FOR REGULATING CORN EAR GRAIN WEIGHT AND YIELD, ENCODED PROTEIN, InDel1 MARKER, EXPRESSION VECTOR AND USE THEREOF IN PLANT TRAIT IMPROVEMENT

CROSS-REFERENCES TO RELATED APPLICATIONS

The present application is a continuation application of International Application No. PCT/CN2023/093126, filed on May 10, 2023, which claims priority to Chinese Patent Application No. 202210524175.7, filed on May 14, 2022. The disclosures of the above-mentioned applications are incorporated herein by reference in their entireties.

REFERENCE TO SEQUENCE LISTING SUBMITTED ELECTRONICALLY

A Sequence Listing is provided herewith as a Sequence Listing XML, "SEQUENCE LISTING.xml" created on May 9, 2025 and having a size of 41,215 bytes. The contents of the Sequence Listing XML are incorporated by reference herein in their entirety.

TECHNICAL FIELD

The present application relates to the technical field of biological genetic engineering, and in particular, to a gene KWE2 for regulating corn ear grain weight and yield, an encoded protein, an InDel1 marker, an expression vector and a use thereof in improving plant traits.

BACKGROUND

As the world's largest food crop, an important feed and industrial raw material, corn (*Zea mays* L.) plays an important role in ensuring food security in the world and in China (Gore et al., 2009; Prasanna 2012). In recent years, with the adjustment of China's agricultural production structure, the area planted with corn has been continuously decreasing. At the same time, due to the rapid development of the animal husbandry and deep processing industries, the consumer demand for corn has increased sharply, and the market demand has shown explosive growth. In particular, the recent COVID-19 epidemic and international turmoil have made food security issues increasingly prominent. In 2020, the average yield of corn in China is 421 kg/666.7 $m^2$, which is only 60% of the average yield of corn in the United States (735 kg/666.7 $m^2$). There is still a lot of room for improvement. Therefore, with limited arable land, significantly increasing corn yield per unit area is the primary task to increase total output, get rid of dependence on imported corn as soon as possible, resolve the contradiction between corn supply and demand, and ensure food security.

The ear number per mu (1 mu≈0.0667 hectares), kernel number per ear, and 100-kernel weight are the three factors that constitute corn yield. Under a specific planting density, the kernel number per ear and hundred kernel weight determine the corn yield per unit area (Lopez-Reynoso and Hallauer 1998). The kernel number per ear is composed of kernel row number (KRN) and kernel number per row (KNR). The KRN genes that have been cloned and analyzed for their functions, such as KRN2 encoding the WD40 protein, negatively regulate the yield of corn and rice by synergizing with the unknown functional protein DUF1644, and have no negative effects on other agronomic traits (Chen et al., 2022). KRN4, located in the intergenic spacer region 60 Kb downstream of the SBP-box gene Unbranched3 (UB3), is a distal regulatory element of UB3, and its knockout mutant KRN and increases in an ear thickness (Liu et al., 2015). KRN1, which encodes an AP2 domain protein, is homologous to the key wheat domestication gene Q. The up-regulated expression of this gene increases the number of paired spikelet meristems and the KRN (Wang et al., 2019). KRN5 (Zm00001d016075) negatively regulates KNR, and also has a certain negative regulatory effect on the kernel number per ear and ear grain weight (An et al., 2022). The cloned ear length qEL7 gene encodes 1-aminocyclopropane-1-carboxylate oxidase 2 and negatively regulates spikelet number, floret fertility and ear length through ethylene signaling. Knocking out this gene can increase the panicle grain weight of hybrids by 13.4% (Ning et al., 2021). KNR6, which controls corn row kernel number, encodes a serine/threonine protein kinase and affects ear length and row kernel number by phosphorylating its interacting protein GTPase activating protein (AGAP). Deletion of the transposon in its promoter region can significantly increase yield (Jia et al., 2020). The candidate gene for ear length QTL (YIGE1) encodes an unknown protein that regulates corn yield by affecting the number of pistil florets. Overexpression of YIGE1 increases the size of the panicle inflorescence meristem, increases ear length and row grain number, thereby increasing corn yield (Luo et al. al., 2022). The gene controlling the ear apical degeneration mutant (ear apical degeneration1, ead1) encodes an aluminum-activated malate efflux transporter protein. Overexpression of this gene can significantly increase ear length and row grain number (Pei et al., 2022).

Although the cloning and functional analysis of these genes provide important genetic resources for the breeding of new high-yield corn varieties, yield-related traits are all quantitative traits and are controlled by a few major-effect genes and multiple minor-effect genes. The functional genes currently obtained are very few. In order to elucidate the molecular mechanism of yield formation and provide excellent genetic resources for the breeding of new corn varieties, it is still necessary to further explore more yield-related trait genes and analyze their utilization pathways.

The information disclosed in this Background section is merely intended to enhance an understanding of the general background of the present application and should not be construed as an admission or in any way implying that the information constitutes related art that is already known to those skilled in the art.

SUMMARY

Based on 1×9801 and the Chang7-2 near isogenic line of 1×9801, the inventor cloned the gene KWE2 that controls corn ear grain weight and yield (kernel row number and kernel number per row are collaboratively determined), and provided a way to utilize it. The molecular marker InDel1 was developed; the KWE2 gene and its rice homologous gene were knocked out by CRISPR/Cas9, and the knockout mutant (KN5585 background) and Ma insertion mutant (W22 background) were used to cross with conventional inbred lines to clarify the yield-increasing effect of the KWE2 gene on hybrids. Based on the homologous genes of corn KWE2 in rice, tobacco, and *Arabidopsis*, the corresponding knockout mutations were created and its performance on the ear-grain weight trait and its effect on yield improvement were clarified. The present application provides technical support for using the KWE2 gene to improve the yield of various crops.

One of the purposes of the present application is to provide a new DNA sequence and cDNA sequence of the gene KWE2 that regulates corn ear grain weight and yield, and the amino acid sequence of the functional protein encoded by the gene KWE2. The gene encodes a SKP1-interacting partner 15 protein, and the down-regulated expression or knockout of this gene increases ear grain weight and yield.

A first aspect of the present application relates to a DNA sequence of the gene KWE2 for regulating the corn ear weight and yield, which is an isolated polynucleotide sequence, including a nucleotide sequence selected from the following group consisting of:

(1) a DNA molecule shown in SEQ ID NO. 1 or SEQ ID NO. 2 (cloned from the genomic DNA of the corn inbred lines Chang 7-2 and 1×9801 respectively);

(2) a cDNA molecule shown in SEQ ID NO.3 (cloned from the corn inbred line B73);

(3) a DNA molecule that can affect the phenotype of yield-related traits, formed through substitutions and/or insertions and/or deletions of one to several base and insertion/deletion/shift/inversion of large fragments nucleotide sequence, on the basis of SEQ ID NO.1, SEQ ID NO.2 or SEQ ID NO.3;

(4) a nucleotide sequence that can hybridize with the nucleotide sequence of SEQ ID NO.1, SEQ ID NO.2 or SEQ ID NO.3 under moderately stringent hybridization conditions and affect yield-related traits; and (5) a nucleotide sequence that has more than 80% homology with the nucleotide sequence of SEQ ID NO.1, SEQ ID NO.2 or SEQ ID NO.3 and affects yield-related traits.

A second aspect of the present application aims to provide a protein encoded by the above-mentioned gene KWE2 for regulating corn ear grain weight and yield, including an amino acid sequence selected from the following group consisting of:

(1) a protein consisting of the amino acid sequence encoded by SEQ ID NO.1, SEQ ID NO.2 or SEQ ID NO.3, as shown in SEQ ID NO.4;

(2) a protein with SEQ ID NO.4 that has undergone substitution, deletion and/or addition of one or several amino acid residues and has affect yield-related traits;

(3) An amino acid sequence that has more than 70% homology with the amino acid sequence of SEQ ID NO. 4 and affects yield-related traits.

A third aspect of the present application relates to a promoter sequence for the expression of the above-mentioned gene KWE2 for regulating corn ear grain weight and yield, which includes a nucleotide sequence selected from the following group consisting of:

(1) the promoter sequence is the DNA sequence shown in SEQ ID NO.5, SEQ ID NO.6 or SEQ ID NO.7, which has the function of specifically initiating the transcription of the gene sequence shown in SEQ ID NO.1 and SEQ ID NO.2 or SEQ ID NO.3 in plants. SEQ ID NO.5 is the promoter sequence in the Chang7-2 donor in the 1×9801 background, and SEQ ID NO.6 is the promoter sequence in 1×9801, SEQ ID NO.7 is the promoter sequence in B73. Compared with SEQ ID NO.5, SEQ ID NO.6 lacks a 209 bp fragment (including a 103 bp PIF_Harbinger_TIR_transposon). Compared with SEQ ID NO.5, SEQ ID NO.7 inserts a 1596 bp fragment (containing an 846 bp helitron and a 407 bp helitron).

(2) the nucleotide sequence that can affect the transcription level of SEQ ID NO.1, SEQ ID NO.2 or SEQ ID NO.3, formed by through substitutions and/or insertions and/or deletions of one to several base as well as insertion/deletion/shift/inversion of large fragments of nucleotide sequences, on the basis of SEQ ID NO.5, SEQ ID NO.6 or SEQ ID NO.7.

A fourth aspect of the present application relates to a recombinant expression vector, an expression cassette, a transgenic cell line or a recombinant bacteria containing the gene and/or promoter.

A fifth aspect of the present application relates to a method and effect of providing the recombinant expression vector, the expression cassette, the transgenic cell line or the recombinant bacteria of the above gene and/or promoter for improving corn, rice, wheat and other plants. Plants that can be transformed in the present application can be monocotyledonous and dicotyledonous plants, including but not limited to corn, wheat, barley, rye, rice, rapeseed cotton, sweet potato, sunflower, potato, soybean, pea, endive, lettuce, cabbage, cauliflower, onion, garlic, spinach, Chinese cabbage, pak choi, cabbage, radish, pumpkin, apple, pear, strawberry, pineapple, tomato, sorghum, carrot, eggplant, cucumber, zucchini, poplar, paper towel, paulownia, switchgrass, alfalfa, peony, Chinese rose, rose, chrysanthemum, *Arabidopsis*, etc.

A sixth aspect of the present application relates to a method for improving plant traits using the KWE2 gene. The method includes preparing the plant containing the recombinant expression vector, the expression cassette, the transgenic cell line or the recombinant bacteria of the gene and/or promoter of the present application, or appropriately adjusting the expression level of the KWE2 gene in the plant, or appropriately changing biological activity of the KWE2 protein, or crossing the plant containing the KWE2 gene that regulates corn ear grain weight and yield according to the present application with another plant. The traits include improved yield and enhanced hybrid vigor in plants that produce or knock out the KWE2 gene that regulates corn ear weight and yield.

One or more technical solutions in the embodiments of the present application have at least any of the following technical effects or advantages.

The KWE2 gene, which regulates corn ear grain weight and yield, is cloned, the functional nucleotide sequence that causes the differential expression of the KWE2 gene is identified, the functional molecular marker InDel1 is developed and the use is provided. On the other hand, the KWE2 gene is knocked out by CRISPR/Cas9, and the knockout mutant (KN5585 background) and Mu insertion mutant (W22 background) are used to cross with conventional inbred lines to clarify the effect of KWE2 gene on hybrid vigor performance of traits such as ear grain weight, 100-grain weight, yield, and plant height. Based on the homologous genes of the gene KWB2 in corn, rice and *Arabidopsis*, corresponding knockout mutations is created to clarify its enhance effect on yield improvement and hybrid vigor performance in multiple important agronomic traits, which provides technical support for using KWE2 gene to improve the yield of various crops and regulate hybrid vigor.

Utilizing the gene and method of the present application can facilitate the creation of high-yield breeding materials for crops such as corn, rice, and wheat, shorten the breeding cycle of new crop varieties, reduce breeding costs, and improve breeding efficiency.

BRIEF DESCRIPTION OF THE DRAWINGS

FIG. 3 is a schematic diagram of the editing of a corn knockout mutant KWE2 gene according to an embodiment of the present application (top to bottom, SEQ ID NOs. 8-12).

FIO. 6 is a phenotypic diagram of the test-cross progeny of the corn knockout mutant according to an embodiment of the present application, bar=20 cm.

Figure 7:
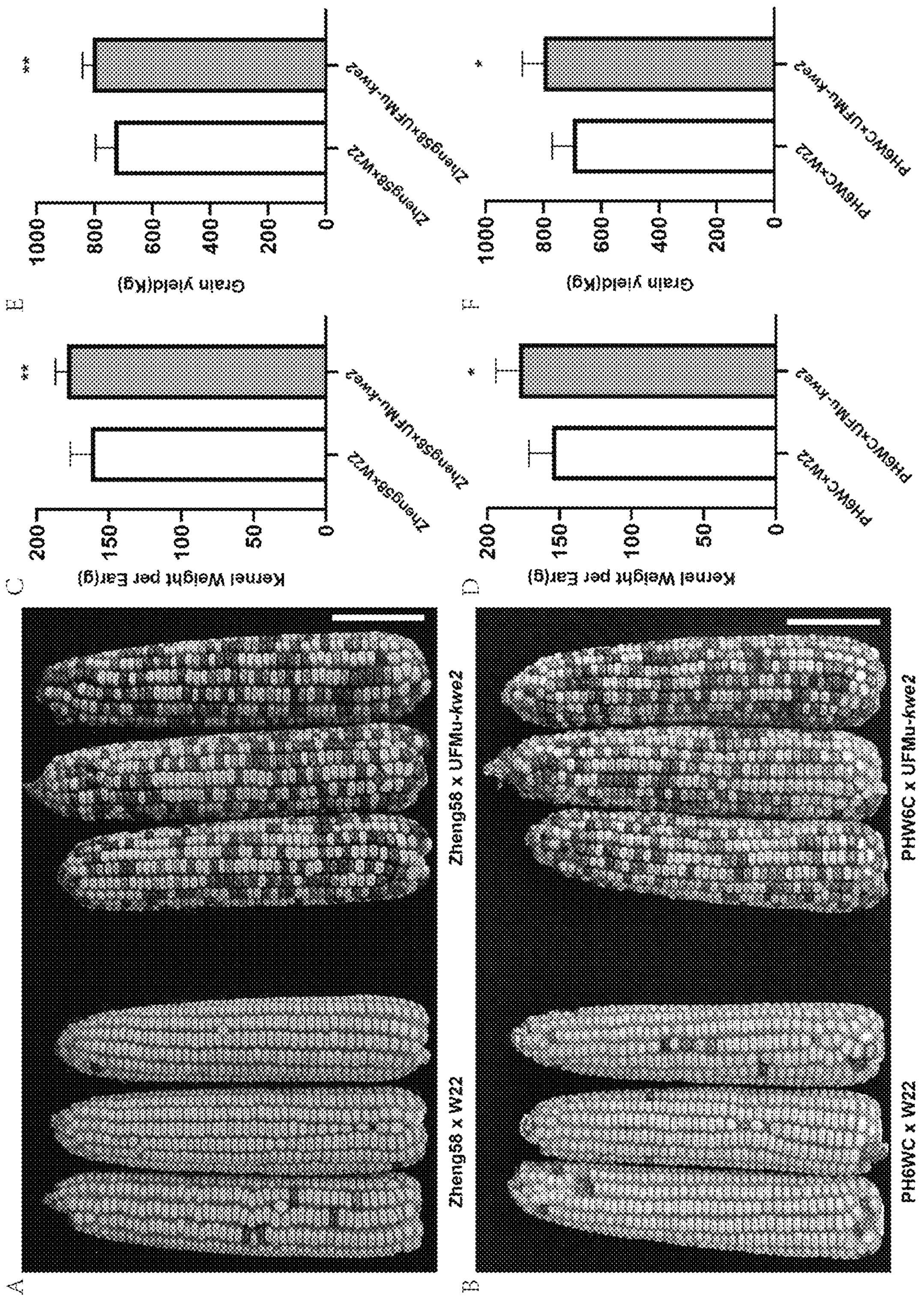

FIG. 7 is a comparison diagram of the grain weight and yield per ear of the test-cross progeny of the corn Mu mutant according to an embodiment of the present application, bar=5 cm.

Figure 8:
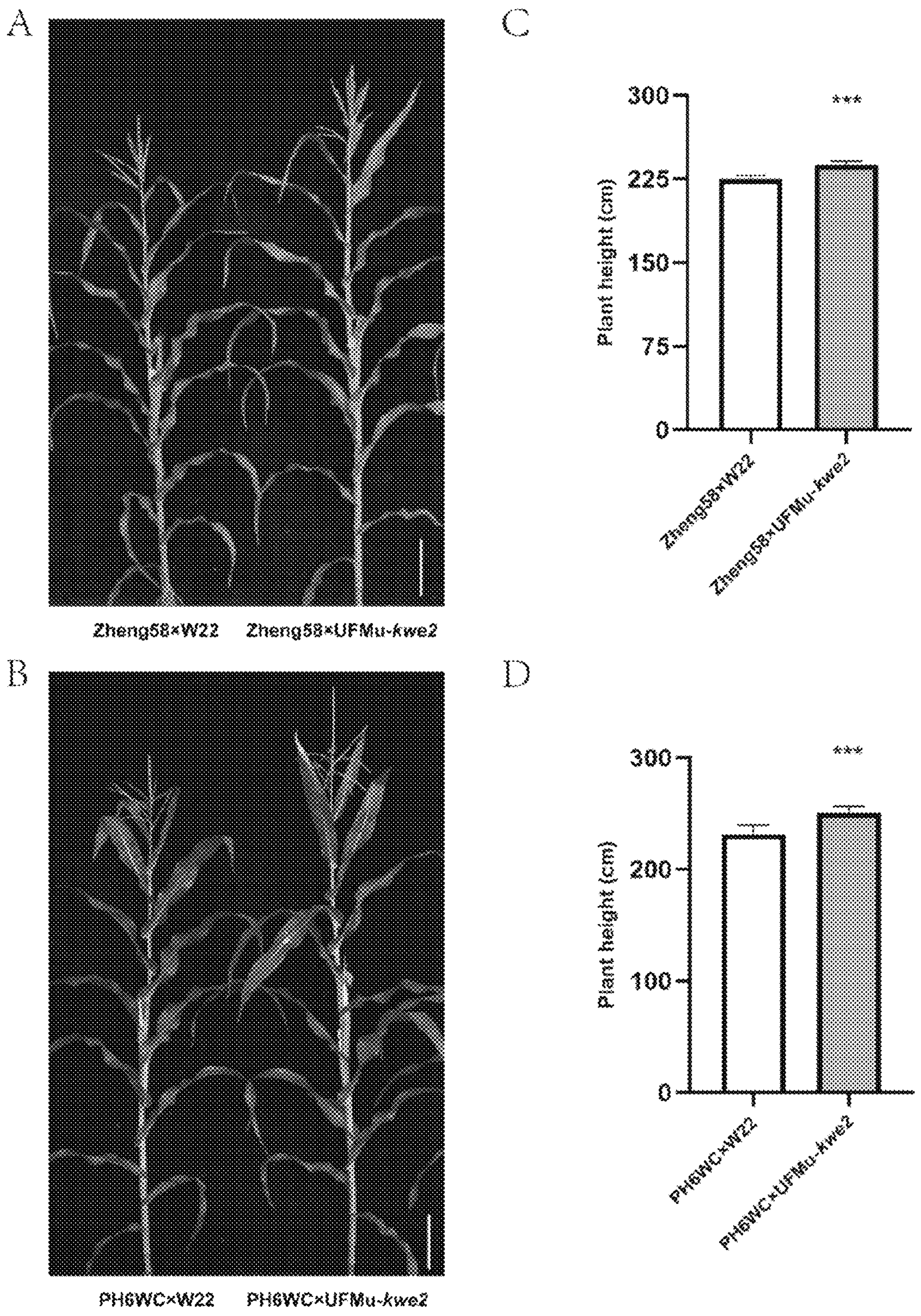

FIG. 8 is a phenotypic diagram of the test-cross progeny of the corn Mu mutant according to an embodiment of the present application, bar=20 cm.

FIG. 9 is a diagram of a rice CRISPR-Cas9 knockout vector and overexpression vector according to an embodiment of the present application.

Figure 10:
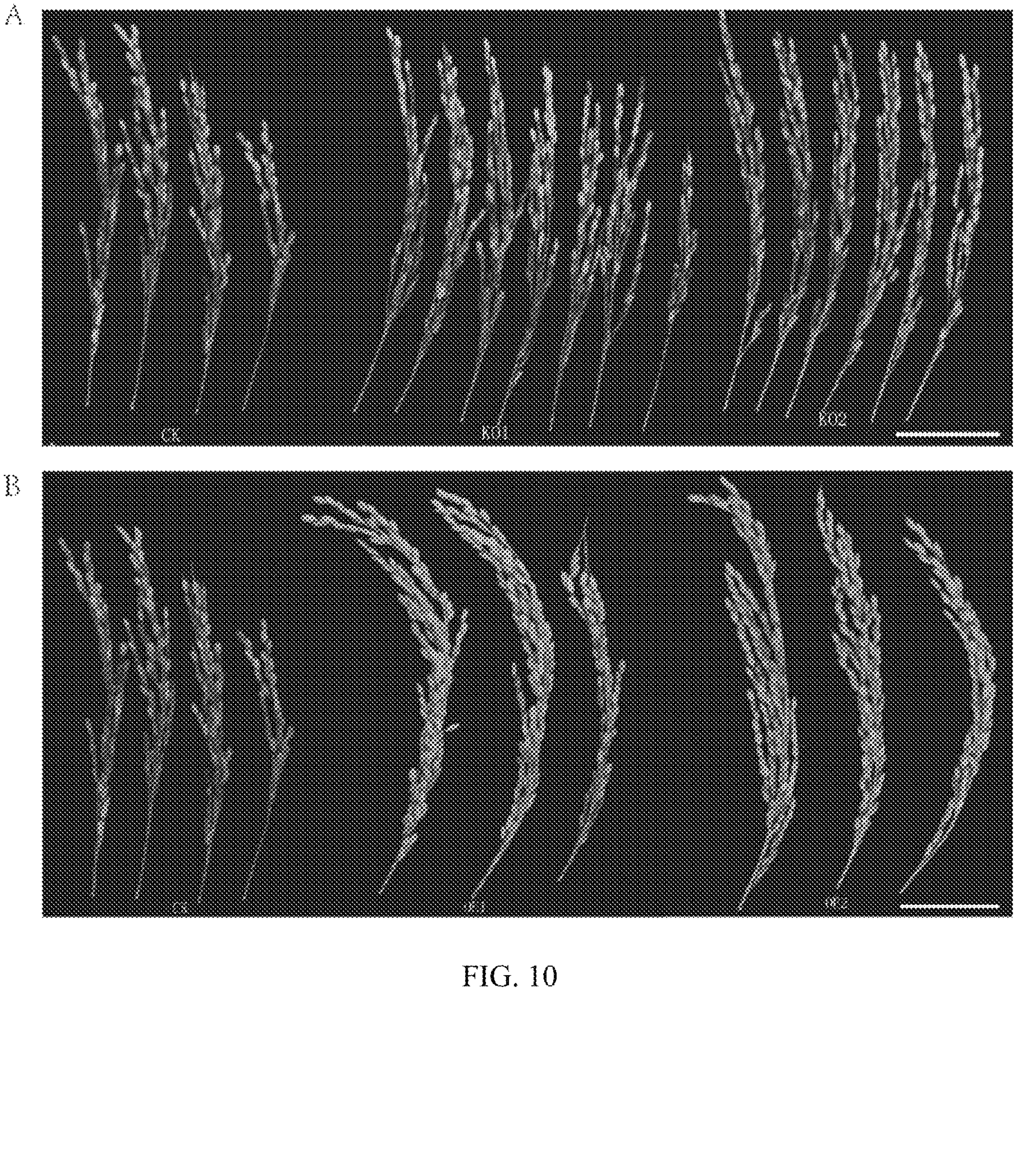

FIG. 10 is a diagram of the panicle phenotype of the knockout and overexpression lines of the rice KWE2 homologous gene according to an embodiment of the present application, bar=5 cm.

Figure 11:

FIG. 11 is a phenotypic diagram of the EMS strain of the *Arabidopsis thaliana* KWE2 homologous gene according to an embodiment of the present application.

DETAILED DESCRIPTION OF THE EMBODIMENTS

Definitions and Explanations of Related Terms

The term "ear grain weight and yield regulatory gene" refers to a nucleotide sequence with the ability to encode a protein, which specifically encodes a protein active polypeptide with the function of regulating ear-grain weight and yield, such as NO. 803-2032 nucleotide sequence of SEQ ID NO. 1 and its degenerate sequence, NO. 733-1962 nucleotide sequence of SEQ ID NO. 2 and its degenerate sequence, and NO. 203-1432 nucleotide sequence of SEQ ID NO. 3 and its degenerate sequence.

The term "degenerate sequence" refers to a sequence in which one or more codons in the nucleotide sequence located in the coding frame of SEQ ID NOs. 1-3 are replaced by degenerate codons encoding the same amino acid. Due to the degeneracy of codons, most degenerate sequences with as low as 70% homology to the coding frame nucleotide sequence of SEQ ID NOs. 1-3 can also encode amino acid sequence encoded by SEQ ID NOs. 1-3.

The "ear grain weight and yield regulatory genes" also include nucleotide sequences that can hybridize with the nucleotide sequences of SEQ ID NOs. 1-3 under moderately stringent conditions or under more highly stringent conditions. Moderately stringent conditions can include hybridization and membrane washing at 65 °C in a solution of 0.1×SSPE (or 0.1×SSC) and 0.1% (w/v) SDS.

The "genes that regulate ear grain weight and yield" also include at least 70% homology with the nucleotide sequences of SEQ ID NOs. 1-3, preferably 80%, 82%, 85%, 86%, 88%, 89% homology, more preferably 90%, 91%, 92%, 93%, 94% homology, the best has at least 95%, 96%, 97%, 98%, 99% homology to nucleotide sequences.

The "gene for regulating ear grain weight and yield" also include variant forms of the SEQ ID NOs. 1-3 open reading frame sequences that encode proteins with the same function as the natural gene KWE2 for regulating ear grain weight and yield. These variant forms include but are not limited to: deletion, insertion and/or substitution of one or several nucleotides, and addition of several nucleotides (usually within 60, preferably within 30, more preferably within 10, the best is within 5) at 5' or 3' end.

The "gene for regulating ear grain weight and yield" also includes the ability to translate a type of amino acid sequence that has the function of regulating corn ear grain weight and yield, such as the amino acid sequence of SEQ ID NO. 4. This type of amino acid sequence also includes a variant form of SEQ ID NO. 4 that has the same function of naturally regulating corn ear grain weight protein. These variant forms include but are not limited to: deletion, insertion and/or substitution of one or several amino acids, and addition of one or several (usually within 20, preferably within 10, more preferably within 5) amino acids at the C-terminal and/or N-terminal. In this field, substitution with amino acids with same or similar properties usually does not change the function of the protein; adding one or several amino acids at the C-terminal and/or N-terminal usually does not change the function of the protein.

The "gene for regulating ear grain weight and yield" also includes the nucleotide sequence that can regulate the expression levels of corn ear grain weight and yield genes, such as the nucleotide sequences of SEQ ID NOs. 5-7. This type of nucleotide sequence also includes variant forms of SEQ ID NOs. 1-3 that can affect the expression level of ear grain weight and yield gene KWE2. These variant forms include, but are not limited to: substitutions and/or insertions and/or deletions of one to several base, as well as insertions/deletions/shifts/inversions of large fragments of nucleotide sequence.

In addition, the full-length nucleotide sequence of the "gene for regulating ear grain weight and yield" or its fragment can usually be obtained by PCR amplification, recombination or artificial synthesis. For the PCR amplification method, corresponding primers can be designed based on the relevant nucleotide sequences disclosed in this example, especially the open reading frame sequence, and can be amplified to relevant sequences using commercially available cDNA library or cDNA library prepared according to conventional methods known to those skilled in the art as a template. When the sequence is long, two or more nested PCR amplifications are usually required, and then the PCR amplification products are spliced together in the correct order. Once the relevant sequences are obtained, recombination can be used to obtain the relevant sequences in large quantities. It is usually cloned into a vector, and then the relevant sequence is isolated from the proliferating host cells through conventional methods such as cell transformation. In addition, mutations can also be introduced into the protein sequences in the embodiment through chemical synthesis. In addition to recombination, fragments of the proteins in the embodiment can also be produced by direct synthesis of polypeptides using solid phase techniques. Protein synthesis in vitro can be done manually or automatically. Each fragment of the protein in the embodiment can be chemically synthesized separately and then connected using chemical methods to produce a full-length protein molecule.

Particularly preferred is at least one protein of the gene KWE2 for regulating the corn ear grain weight and yield disclosed in the present application expressed in a higher plant. Once the desired nucleotide sequence is transformed into a specific plant species, it can be propagated in that species or transferred into other varieties of the same species (especially including commercial varieties) using conventional breeding techniques. The nucleotide sequence of each gene KWE2 for regulating corn ear grain weight and yield disclosed in the present application can be inserted into an expression cassette, or included in a non-pathogenic self-replicating virus, and then preferably, the expression cassette is stably integrated into the plant genome. Plants transformed in the present application can be monocotyledonous and dicotyledonous plants, including but not limited to corn, wheat, barley, rye, rice, rapeseed, cotton, sweet potato, sunflower, potato, bean, pea, chicory, lettuce, cabbage, cauliflower, onion, garlic, spinach, Chinese cabbage, Chinese cabbage, cabbage, radish, pumpkin, apple, pear, strawberry, pineapple, tomato, sorghum, carrot, eggplant, cucumber, zucchini, poplar, paper towel, paulownia, switchgrass, alfalfa, peony, rose, rose, chrysanthemum, *Arabidopsis*, etc. By expressing the nucleotide sequence disclosed in the present application in transgenic plants, the biosynthesis of functional proteins capable of enhancing the corresponding heterosis performance is promoted in transgenic plants. In this way, transgenic plants with enhanced heterosis performance can be produced. In order to express the nucleotide sequences of the present invention in transgenic plants, the nucleotide sequences disclosed in the present application may need to be modified and optimized. All organisms have specific codon usage preferences, which are known in the art. It is possible to change the codons of the nucleotide sequence described in the present application to match plant preferences while maintaining the amino acids encoded by the nucleotide sequence. Moreover, encoding sequences with at least about 35% GC content, preferably more than about 45%, more preferably more than 50%, and most preferably more than about 60% GC content can best achieve high-level expression in plants. Furthermore, high levels of expression in plants are best achieved from coding sequences having a GC content of at least about 35%, preferably more than about 45%, more preferably more than 50%, and most, preferably more than about 60%.

Some specific embodiments of the present application will be described in detail below. The following embodiments will facilitate a better understanding of the present application, but it should be understood that the scope of the present application is not limited by the specific embodiments. Based on the embodiments of the present application, all other embodiments obtained by those skilled in the art without any creative effort shall fall within the scope of the present application. The experimental methods described in the embodiments of the present application, unless otherwise specified, are all routine methods. Those skilled in the art should understand that, unless otherwise specified, the reagents, enzymes, etc. used in the following examples are all analytical pure grade reagents or enzymes that can be purchased from reagent companies. The materials, methods, and examples are illustrative only and are not intended to be limiting.

Example 1. Cloning and Functional Verification of Gene KWE2

A major regulatory gene KWE2 that affects the ear grain weight and yield of hybrids was identified in 1×9801 and the Chang 7-2 near-isogenic line SSSL168 of 1×9801. The candidate gene was located in the 40 kb physical interval of corn chromosome 2 through map-based cloning, there are two protein-coding genes Zm00001eb076040 (Zm00001d002881) and Zm00001eb076050 (Zm00001d002882) in this interval in the B73 reference genome.

Figure 1:
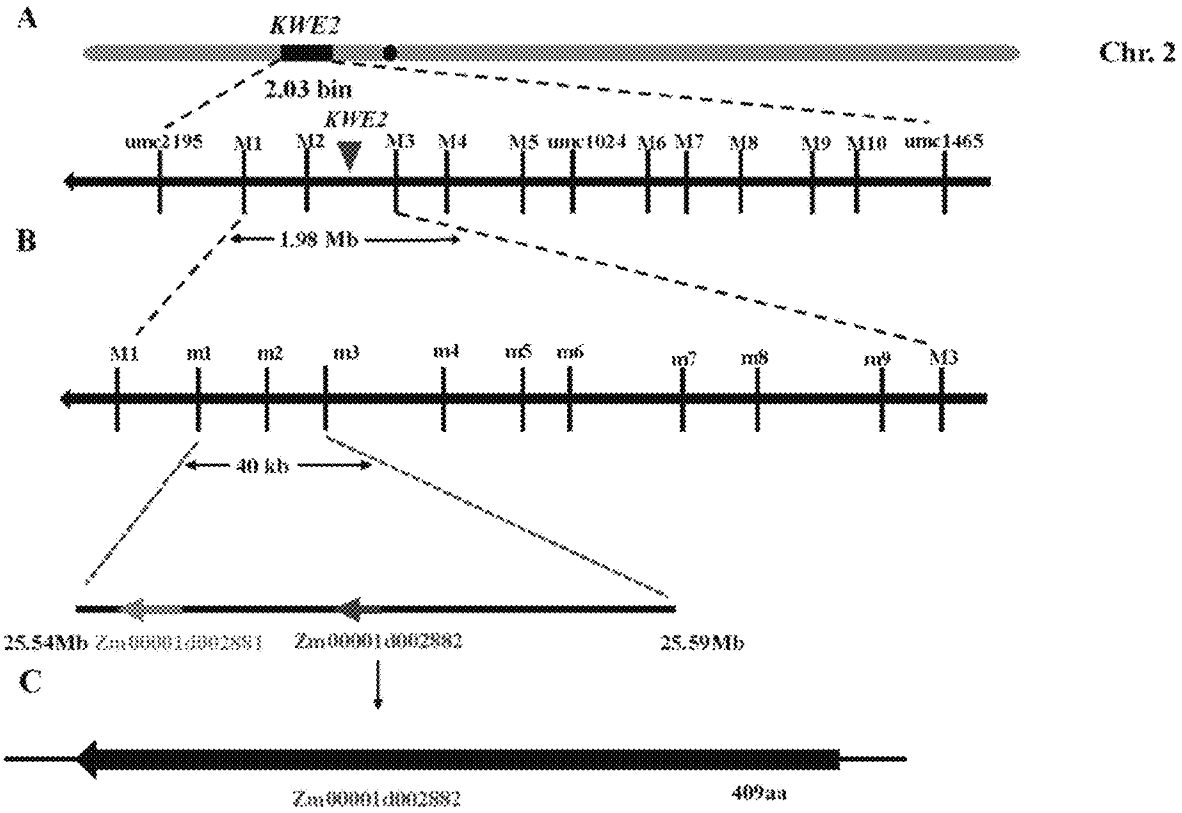
FIG. 1 is a schematic structural diagram of a KWE2 gene according to an embodiment of the present application.

Sequencing analysis of the two candidate genes found that there were no amino acid sequence differences in the coding regions of the two genes. Only the promoter region of the Zm00001eb076050 gene bad a long fragment insertion deletion. The promoter sequence in the Chang7-2 (Chang7-2) near-isogenic line (1×9801KWE2) of 1×9801 has a 209 bp fragment (including a 103 bp PIF_Harbinger_TIR_transposon) inserted compared to 1×9801. The promoter sequences in B73 and Zheng58 have a 1596 bp inserted fragment (including a 846 bp helitron and a 407 bp helitron) compared to 1×9801KWE2. Therefore, this gene was identified as a candidate gene related to ear grain weight and yield. Its functional annotation showed that Zm00001eb076050 encodes a SKP1-interacting partner 15 protein, with a full-length coding region of 1230 bp and no introns (see FIG. 1).

Figure 2:
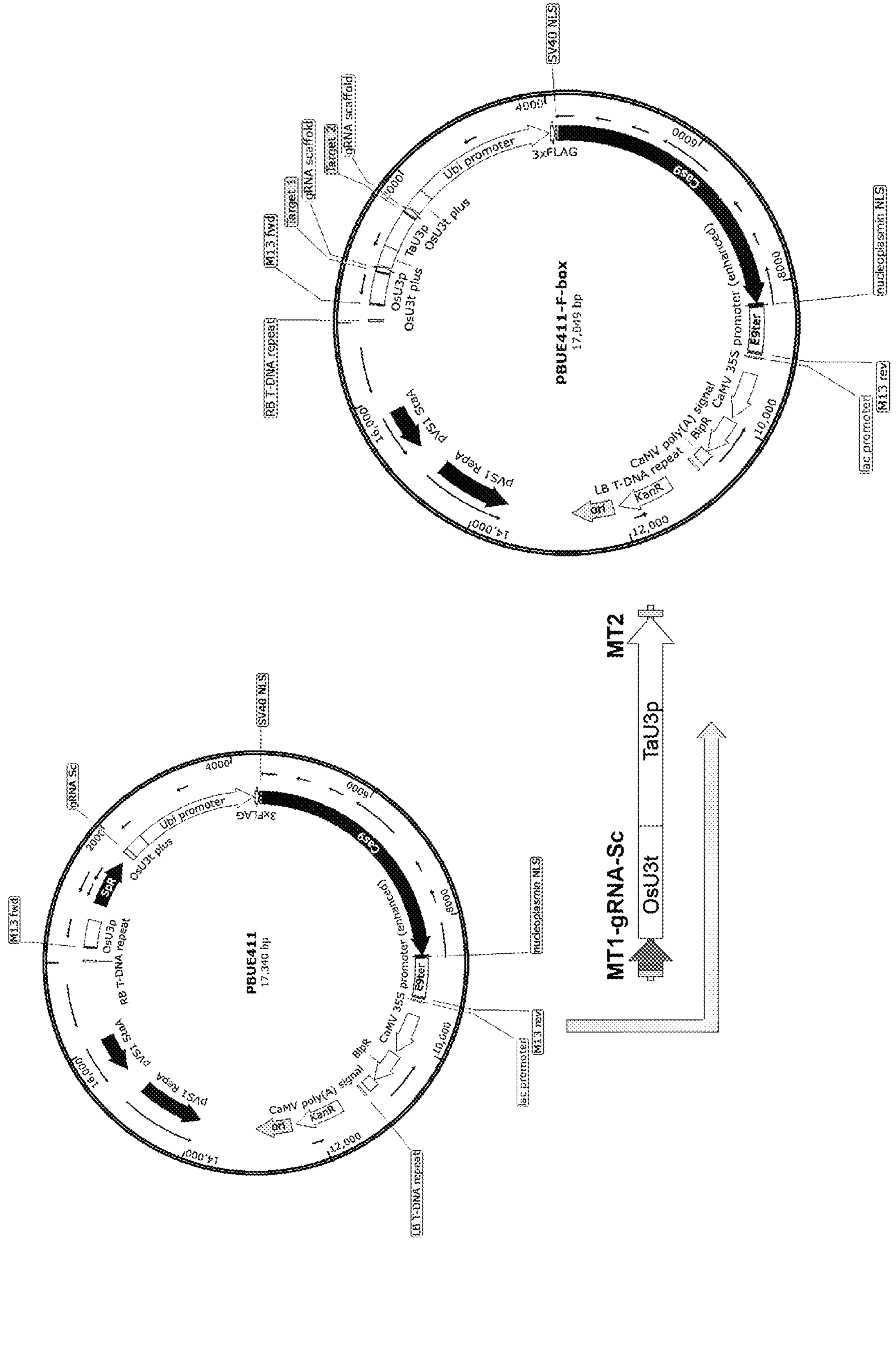
FIG. 2 is a construction diagram of a KWE2 gene CRISPR-Cas9 knockout vector according to an embodiment of the present application.

In order to verify the function of this gene, two target sites (Target) and Targat2) were designed on the first exon of the KWE2 gene, and pCBC-MT1T2 was used as a template to amplify them using two primer pairs (MT1T2-F, MT1T2-F0, MT1T2-R0, MT1T2-R), connect the target site to the final vector pBUE411 to complete the construction of the CRISPR-Cas9 knockout vector (see FIG. 2), and the immature embryos of the corn inbred line KN5585 were transformed through *Agrobacterium*-mediated transformation.

```
Target1:
                                    SEQ ID NO. 13
TCCTGCCCCGACCCGGCCG (CGG),

Target2:
                                    SEQ ID NO. 14
CTTCTCCTGCCCGCTGGAC (AGG);

MT1T2-F:
                                    SEQ ID NO. 15
AATAATGGTCTCAGGCGTCCTGCCCCGACCCGGCCG,

MT1T2-F0:
                                    SEQ ID NO. 16
GTCCTGCCCCGACCCGGCCGGTTTTAGAGCTAGAAATAGC;

MT1T2-R0:

GTCCAGCGGGCAGGAGAAGCGCTTCTTGGTGCC,
                                    SEQ ID NO. 17
MT1T2-R:
                                    SEQ ID NO. 18
ATTATTGGTCTCTAAACGTCCAGCGGGCAGGAGAAG.
```

The CRISPR-Cas9 vector was transferred into *Agrobacterium* EHA105 by electroporation and identified by PCR. The freshly peeled young embryos of about 1 mm of corn inbred line KN5585 was used as material, and put into a 2 mL plastic centrifuge tube containing 1.8 ml of suspension. Approximately 150 immature embryos were processed within 30 minutes. The suspension was aspirated off, 1.0 ml of *Agrobacterium* suspension was added to the remaining corn embryos in the tube, and leave for 5 minutes. The immature embryos in the centrifuge tube was suspended and poured onto the co-culture medium. A pipette was used to remove excess *Agrobacterium* bacteria from the surface and co-culture for 3 days at 23 °C in the dark. After co-culture, the young embryos were transferred to resting medium, cultured in the dark at 28 °C for 6 days, and then placed on the selection medium containing 5 mg L-1 Bialaphos to select and culture for 2 weeks, then transferred to the selection medium containing 8 mg L-1 Bialaphos to select and culture for 2 weeks. The resistant calli were transferred to differentiation medium 1 and cultured at 25 °C under 5000 Lx light for 1 week. Then transfer the callus to differentiation medium 2 and culture it under light for 2 weeks; transfer the differentiated seedlings to rooting medium and culture them under 25 °C 5000 Lx light until they take root; transfer the seedlings to small pots for growth, transplant them to the greenhouse after a certain growth stage, and harvest the offspring seeds after 3-4 months.

Figure 4:
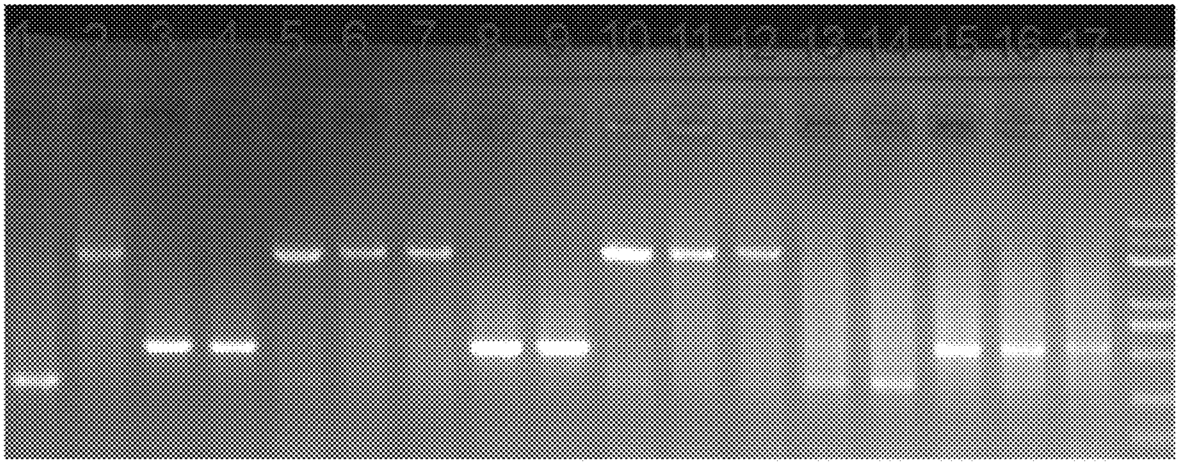
FIG. 4 is a distribution diagram of InDel1 in inbred lines according to an embodiment of the present application; lanes 1-17 respectively represent inbred ensemble 3 (Zong3), Qi319, Yadan 888 male parent (T4691), Yudan 888 female parent (15S717), Dan340, B73, Zheng58, Chang7-2, PH4CV, PH6WC, C8605, U8112, 7884-4Ht, 1×9801, 1×9801$^{KWE2}$, Jing724, and Shen5003.

Knockout events were identified in the T2 generation (see FIG. 3), and homozygous knockout mutants were obtained. In order to clarify the yield-increasing effect of KWE2 gene in different genetic backgrounds, three homozygous knockout mutants were randomly selected and crossed with inbred lines Qi319, Zheng58, PH6WC, Shen5003, etc. of different heterotic groups. Difference analysis of KWE2 gene of inbred lines is shown in FIG. 4:

(1) First, the InDel1 marker primer pair is designed based on the 209 bp difference in the KWE2 gene promoter region of 1×98018WE and 1×9801. Its sequence is as follows:

```
                                        SEQ ID NO. 19
F: 5'-GTCAGCCCAGAACAAACG-3',

                                        SEQ ID NO. 20
R: 5'-GGTCCCACGAGAAGAACG-3';
```

(2) Tissue samples from the inbred line to be identified is taken and genomic DNA is extracted;

(3) The resulting inbred line genomic DNA is used as a template and the InDel1 primer is used to perform PCR amplification;

(4) The length of the amplification product of the primer pair is detected: 515 bp corresponds to the 1×9801KWE2 genotype; 306 bp corresponds to the 1×9801 genotype; and 2111 bp corresponds to the B73 genotype, Inbred lines can be divided into three types through marker analysis. The banding patterns of 7884-4Ht are consistent with 1×9801 and Zong3, the banding patterns of PH4CV, Jing724 and Shen5003 are consistent with 1×9801KWE2 and Chang7-2, and the banding patterns of Dan340, Qi319, PH6WC, C8605 and U8112 are consistent with Zheng58 and B73.

Figure 5:
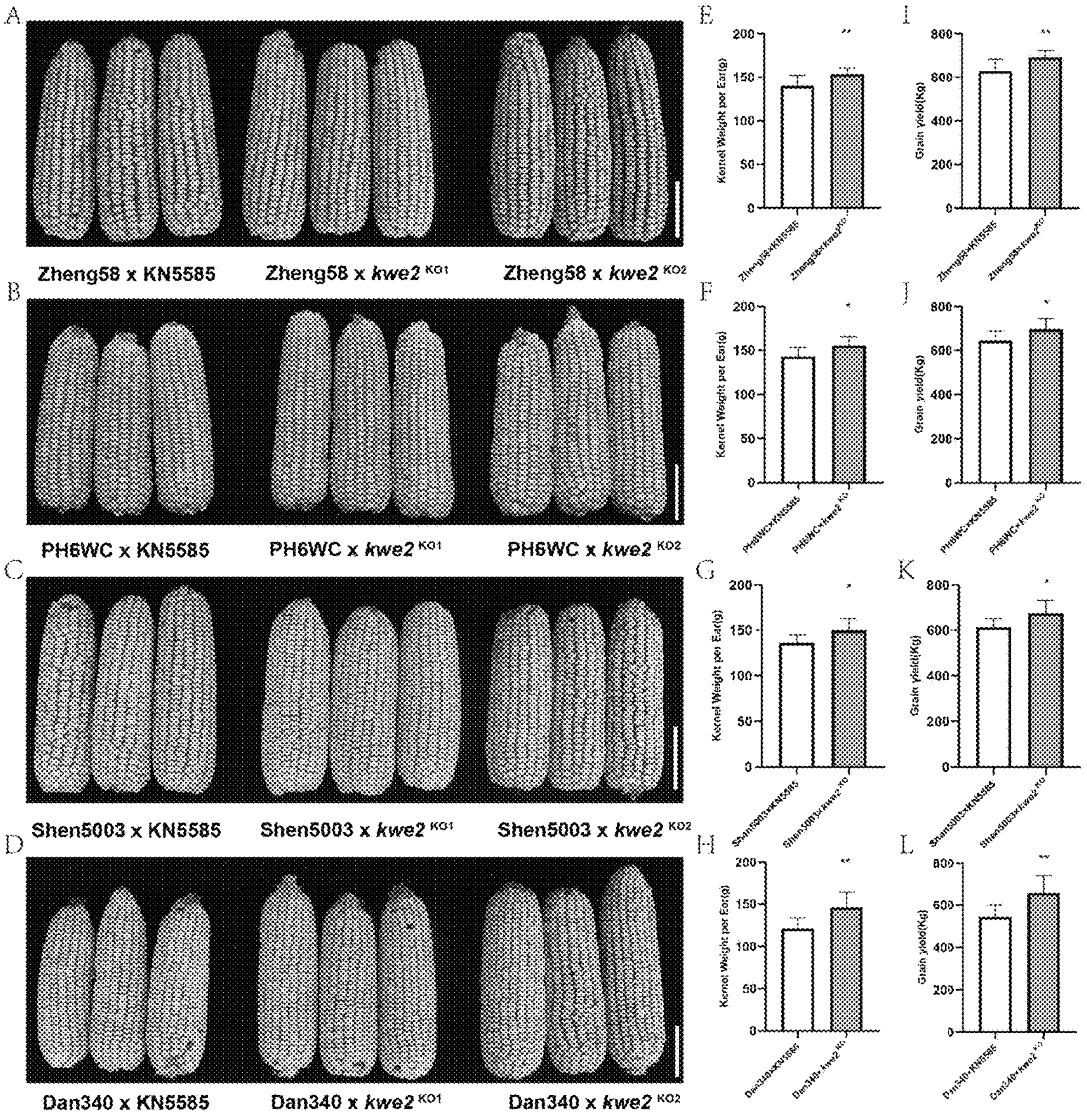
FIG. 5 is a comparison chart of the grain weight and yield per ear of the test-cross progeny of the corn knockout mutant according to an embodiment of the present application, bar=5 cm.
Figure 6:
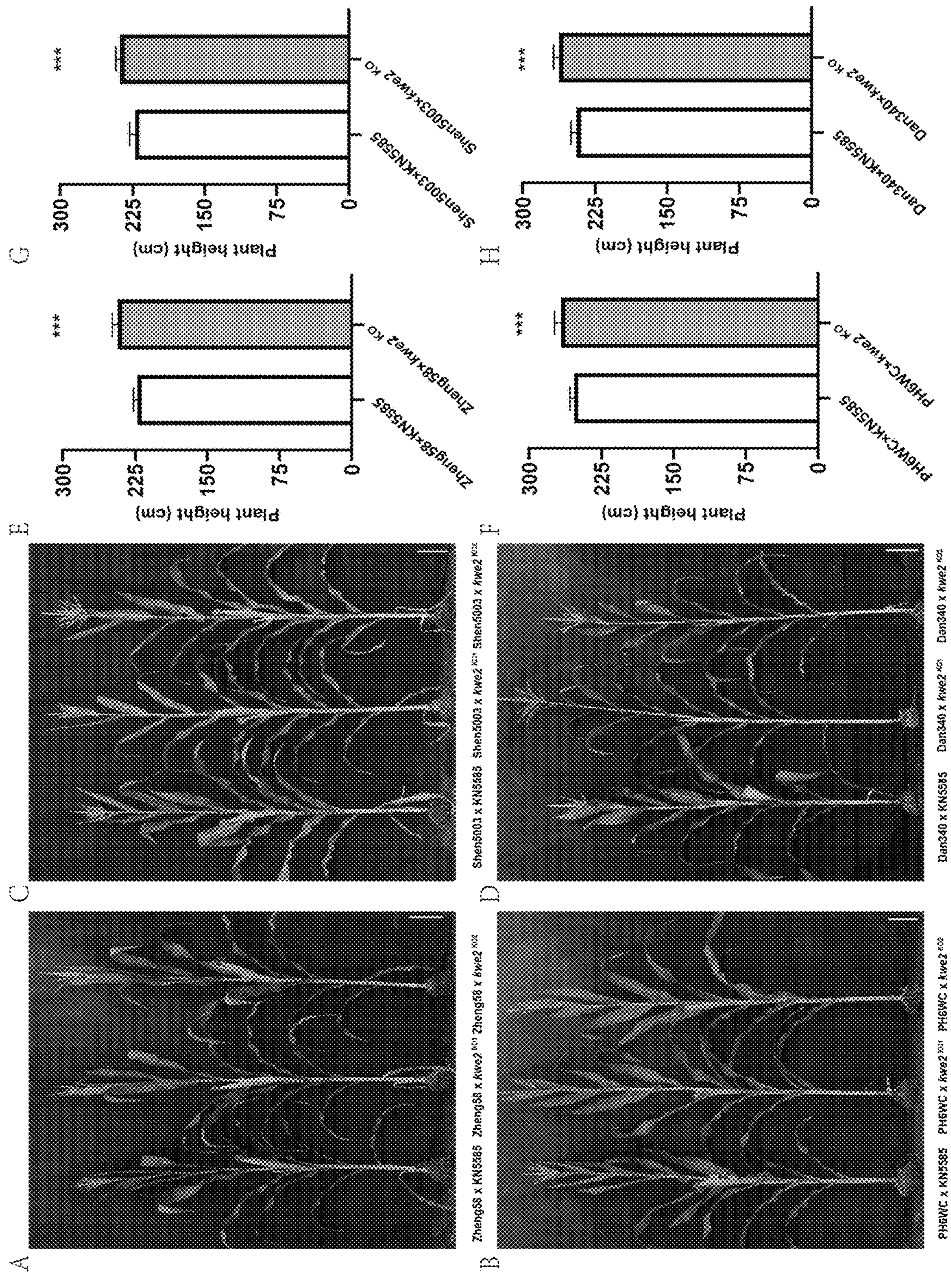

The above-mentioned hybrid combinations were planted at the transgenic base of the Henan Academy of Agricultural Sciences. At the same time, the hybrids of the transformation receptor KN5585 and these inbred lines were used as controls to conduct field identification of each hybrid combination. The identification results showed that the F1 hybrid between the knockout mutant and the inbred line had significantly higher traits such as ear grain weight and yield than the hybrid combination of KN5585 and the respective inbred lines (see FIG. 4 and FIG. 5). At the same time, the UFMu insertion mutant of the KWE2 gene (W22 background) in the American resource library was identified and purified and then crossed with the above-mentioned inbred lines, and its phenotypes were field identified in Hebi and Yuanyang in 2020. It was found that compared with the hybrid combination of W22 and the respective cross lines, the characteristics such as ear grain weight and yield were significantly increased (see FIGS. 6 and 7).

The above results indicate that the down-regulated expression or loss of function of KWE2 is beneficial to the improvement of corn ear weight and yield and the expression of heterosis for other major agronomic traits.

Example 2: Analysis and Verification of the Role of KWE2 Gene in Other Species To clarify whether homologous genes of KWE2 in other species have similar effects, CRISPR-Cas9 knockout of the homologous gene of KWE2 in rice was performed.

The specific operations are as follows:

1. Constructing the CRISPR-Cas9 vector of rice KWE2 gene cDNA (FIG. 9A), designing dual-target gRNA in the exon region (target 1: ccgataagctgcggcaatgccgg, target 2: aggacgggaggagcaaatcccgg), and using VSF-Y1 primer pair and VSF-B1 primer pair to construct intermediate vector. VSF-Y1 reaction system: 2 μL gRNA, 1.5 μL VSF-Y1 empty, 0.5 μL ECO311 endonuclease, 0.5 μL T4-DNA ligase, 1 μL T4 buffer, 4.5 μL $H_2O$, incubate at 37 °C for 2 h. VSF-B1 reaction system: 2 μL gRNA, 1.5 μL VSF-B1 empty, 0.5 μL ECO311 endonuclease, 0.5 μL T4-DNA ligase, 1 μL T4 buffer, 4.5 μL $H_2O$, incubate at 37 °C for 2 h. PCR reaction program: 95 °C for 10 min, 55 °C for 10 min, 14 °C for 5 min.

```
VSF--Y1 primer:
VSF--Y1 (+):
                                        SEQ ID NO. 21
cagtGGTCTCaggcaccggcattgc cgcagcttat,

VSF--Y1 (-):
                                        SEQ ID NO. 22
cagtGGTCTCaaaacataagctgcggcaatgccgg;

VSF--B1 primer:
VSF--B1 (+):
                                        SEQ ID NO. 23
cagtGGTCTCaggcaggacggaggaggcaaatcc,

VSF--B1 (-):
                                        SEQ ID NO. 24
cagtGGTCTCaaaacggatttgcctcctccgtcc.
```

2. Recombinant plasmid transformation (1) Incubating 5 μL of ligation product with 200 μL of *E. coli* competent cells DH5a on ice for 30 min;

(2) Quickly placing it in a constant temperature water bath at 42 °C and heat shock, conversion for 90 s;

(3) After 2 minutes of ice bath, adding 500 μL LB liquid culture medium and mix well;

(4) Shaking the bacteria at 200 rpm at 37 °C for 45 minutes to restore the cells to normal growth;

(5) Evenly spreading the bacterial solution on the LB solid culture medium plate;

(6) After 30 minutes, placing it in a 37 °C constant temperature incubator for overnight culture.

3. Selection of a single clone to extract plasmid. The specific steps are as follows:

(1) Picking a single clone from the LB solid medium plate and inoculating it into kanamycin-resistant LB liquid medium with a final concentration of 50 μg/mL, and culturing it at 37 °C overnight;

(2) Taking 4 mL of activated bacterial solution, centrifuge at 10,000 rpm for 2 minutes at room temperature, and discard the supernatant completely;
(3) Taking 250 μL of Solution I reagent containing RNase A and resuspend the bacterial clumps thoroughly;
(4) Taking 250 μL Solution II reagent to lyse the bacterial mass, and gently inverting it several times until the bacterial cells are transparent;
(5) Taking 350 μL Solution III reagent and inverting it several times until a white, compact floc is formed;
(6) Centrifuging at 12,000 rpm for 10 minutes at room temperature and taking the supernatant;
(7) Taking out the nucleic acid purification column from the kit and placing it on the collection tube;
(8) Transferring the clarified supernatant from step 6 above to the nucleic acid purification column, centrifuging at 12,000 rpm at room temperature for 1 min, and discard the filtrate;
(9) Adding 500 μL of Buffer W1 to the nucleic acid purification column, centrifuging at 12,000 rpm for 30 s at room temperature, and discarding the filtrate;
(10) Adding 700 μL of Buffer W2 to the nucleic acid purification column, centrifuging at 12,000 rpm for 30 s at room temperature, and discard the filtrate;
(11) Repeating the above steps (10);
(12) Placing the nucleic acid purification column on the collection tube and leaving it at room temperature at 12,000 rpm for 2 minutes to remove as much residual liquid as possible;
(13) Discarding the collection tube, place the nucleic acid purification column in a 1.5 mL EP tube, and adding 50 μL of eluent to elute the DNA attached to the nucleic acid purification column membrane (the eluent can be preheated in a constant temperature water bath at 65 °C to help elute DNA), let stand at room temperature for 2 minutes;
(14) Centrifuging at 12,000 rpm for 2 minutes at room temperature to elute the DNA attached to the nucleic acid purification column membrane, and storing it in a refrigerator at a low temperature of −40 °C;
(15) Taking a trace amount of the recovered product and use agarose gel electrophoresis with a concentration of 1% to detect the quality of the plasmid extraction.
(16) performing single clone sequencing on the plasmid.

4. Dual target enzyme digestion ligation system: 1 μL VSF-Y1-1 (plasmid), 1.5 μL VSF-B1-1 (plasmid), 0.5 μL LguI, 0.5 μL T4 ligase, 1 μL T4 buffer, 5.5 μL $H_2O$, after incubating in an incubator at 37 °C for 2 hours, transforming into *E. coli*, and performing bacterial detection after shaking and culturing.
5. Bacteria detection: 10 μL 2× Mix, 1 μL VSF-Y1+ (forward detection primer), 1 μL GET—(reverse detection primer), 8 μL $H_2O$) for bacterial liquid detection, and the target band is 750 bp. Picking the correct single clone and inoculate the bacteria, extracting and sequencing the plasmid.

```
Reverse detection primer GET-:
                                    SEQ ID NO. 25
ATACGAAGTTATGACTGCGACCGA.
```

6. Taking mature rice seeds, mechanically dehull them, select plump, plaque-free and high-quality seeds, disinfect them and inoculate them onto the corresponding culture medium to induce callus.
7. Picking a single colony of *Agrobacterium*, placing it in the culture medium, and culturing it with shaking.
8. *Agrobacterium* and callus co-culture
① Putting the cultured bacterial liquid into a centrifuge tube, centrifuge to get the supernatant, and prepare *Agrobacterium* suspension;
② Picking out the callus that has grown to a certain size and infect it with *Agrobacterium* suspension;
③ Placing the callus on the co-culture medium.
9. Filter
① Taking out the callus;
② Transferring the dried callus to the screening medium for the first screening;
③ Transducing the initial callus with resistant calli into new culture medium for the second screening.
10. Induction, differentiation and rooting of resistant callus
① Picking the resistant callus, move it into a petri dish containing differentiation medium, seal it with a sealing film, and place it in a constant-temperature culture room to wait for differentiation into seedlings.
② When the seedlings grow to about 1 cm, moving them to the rooting medium to strengthen the seedlings.
11. Extracting plant genomes by CTAB method, and detect positive plants by PCR.

At the same time, the overexpression vector of the rice KWE2 gene (FIG. 9B) was genetically transformed:
① Taking 1 μL of overexpression vector plasmid and add 50 μL of BHA105 *Agrobacterium* competent cells;
② After thoroughly mixing taking the mixture into an electroporation cup for electroporation. After electroporation, adding 1 mL of LB liquid culture medium. Mix thoroughly and transfer to a 1.5 mL Ep tube. Shake and incubate on a shaker at 30 °C and 180 rpm for 30 minutes. Take 50 μL of the activated *Agrobacterium* bacteria liquid and inoculate it on LB solid medium, and cultivate it in the dark at 30 °C for 48 hours.
③ *Agrobacterium* detection primer pair hyg(280)+; SEQ ID NO.26

```
5'ACGGTGTCGTCCATCACAGTTTGCC3';

5'TTCCGGAAGTGCTTGACATTGGGGA3'.
```

hyg(280)−; SEQ ID NO.27
④ Selecting Minghui 86 rice grains with no mildew spots and normal bud openings, disinfect with 75% alcohol for 1 minute, rinse with sterile water, 1 minute/time; disinfect with sodium hypochlorite for 20 minutes, rinse with sterile water 3 times, 1 minute/time: the resulting rice grains were inoculated into the induction medium and cultured under light at 26 °C for 20 days.
⑤ Picking *Agrobacterium* in the infection solution, prepare an *Agrobacterium* resuspension with OD600=0.2, pick the callus in an Erlenmeyer flask, add the *Agrobacterium* resuspension, and discard the bacterial solution after 10-15 minutes of infection. The calli were inoculated into co-culture medium and co-cultured at 20 °C for 48-72 h.
⑥ Inoculating the callus into the screening medium and cultivate it in the dark at 26 °C for 20-30 days; pick the positive callus to the second screening medium. During the callus picking process, be sure to select monoclonal callus and cultivate it in the dark at 26 °C for 7-10 days.
⑦ Inoculating the positive callus into the differentiation medium, and culture it in the light at 25-27 °C for 15-20 days. After differentiation of 2-5 cm buds, inoculate it into the rooting medium, and culture it in the light at 30 °C for 7-10 days, ⑧ Using CTAB method to extract rice genomic DNA, conduct PCR detection, and detect positive seedlings.

The T2 generation of transgenic positive plants was genotyped and homozygous CRISPR-Cas9 mutants and overexpression lines were obtained (FIG. 10). CRISPR-Cas9 knockout of KWE2 can increase the number of tillers and spikelets, while its overexpression reduces tillers and increases the number of spikelets.

It can be seen that the rice KWE2 gene negatively regulates the number of tillers and spikelets, but promotes the increase of ear grain number, thereby affecting the superior performance of hybrid yield.

Example 3: Analysis and Verification of the Role of KWE2 Gene in Dicotyledonous Plants To further clarify the role of KWE2 in dicots, a T-DNA insertion mutant (N666804/SALK_095140C) of the *Arabidopsis* KWE2 homologous gene (At1g76920) was performed phenotypic analysis. T-DNA is inserted into the 5'UTR (Untranslated region) of At1g76920, and the detection primer pair is

```
                                          SEQ ID NO. 28
LP-5'-AGAACAGTACCATGGCGTGAC-3' and

                                          SEQ ID NO. 29
RP-5'-ACGTTCTGTCAAATCTGTCCC-3' .
```

As can be seen from FIG. 11, the plant height, pod length and other traits of the KWE2 T-DNA insertion mutant are significantly better than the wild-type control, indicating that the KWE2 gene also has a role in regulating yield in dicotyledonous plants.

What is claimed is:

1. A primer pair for detecting a 209 bp insertion/deletion fragment in a promoter region of a KWE2 gene, wherein the KWE2 gene comprises a nucleotide sequence selected from SEQ ID NO.1, SEQ ID NO.2 and SEQ ID NO.3, and the primer pair is as follows:

```
                                    SEQ ID NO. 19
F: 5'-GTCAGCCCAGAACAAACG-3',

                                    SEQ ID NO. 20
R: 5'-GGTCCCACGAGAAGAACG-3',
```

wherein the primer pair amplifies a target region spanning the 209 bp insertion/deletion fragment between promoter sequences of SEQ ID NO.5 and SEQ ID NO.6, and SEQ ID NO.5 comprises the 209 bp insertion/deletion fragment that is absent in SEQ ID NO.6.

* * * * *